United States Patent
Eden et al.

(10) Patent No.: US 11,202,843 B2
(45) Date of Patent: Dec. 21, 2021

(54) MICROPLASMA DEVICES FOR SURFACE OR OBJECT TREATMENT AND BIOFILM REMOVAL

(71) Applicant: The Board of Trustees of the University of Illinois, Urbana, IL (US)

(72) Inventors: J. Gary Eden, Champaign, IL (US); Peter Peng Sun, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 532 days.

(21) Appl. No.: 15/981,085

(22) Filed: May 16, 2018

(65) Prior Publication Data
US 2018/0333511 A1     Nov. 22, 2018

Related U.S. Application Data

(60) Provisional application No. 62/508,689, filed on May 18, 2017.

(51) Int. Cl.
*A61L 2/14*     (2006.01)
*B08B 9/045*    (2006.01)
(Continued)

(52) U.S. Cl.
CPC ...... *A61L 2/14* (2013.01); *B08B 1/04* (2013.01); *B08B 9/04* (2013.01); *B08B 9/045* (2013.01);
(Continued)

(58) Field of Classification Search
CPC .... A61L 2/14; A61L 2202/15; A61L 2202/25; A61L 9/22; A61L 2202/11;
(Continued)

(56) References Cited

U.S. PATENT DOCUMENTS

| | | |
|---|---|---|
| 5,876,663 A | 3/1999 | Laroussi |
| 6,563,257 B2 | 5/2003 | Vojak et al. |

(Continued)

FOREIGN PATENT DOCUMENTS

WO   WO-2007087371 A2 *  8/2007  .............. H01J 9/245

OTHER PUBLICATIONS

Boppe et al., "Investigative approach to improve hot water system hydraulics through temperature monitoring to reduce building environmental quality hazard associated to Legionella", Building and Environment, vol. 108, pp. 230-239, Aug. 31, 2016.

(Continued)

*Primary Examiner* — Walter D. Griffin
*Assistant Examiner* — Cameron J Allen
(74) *Attorney, Agent, or Firm* — Greer, Burns & Crain, Ltd.; Steven P. Fallon

(57) ABSTRACT

An air fed mycoplasma device includes an array of elongate microchannels formed in a plastic or ceramic having tolerance to ozone and other radicals formed when plasma is generated from air in the microchannels. The microchannels include inlets configured to accept an air feed, and outlets configured to direct plasma jets toward a surface (which may be flat or internal to a pipe, for example) or object. An array of electrodes within the plastic/ceramic housing is configured to ignite and maintain plasma in the microchannels and is isolated by the dielectric from the microchannels. A supply intake for is configured to providing a plasma medium into the microchannels.

24 Claims, 22 Drawing Sheets

(51) Int. Cl.
  *B08B 1/04* (2006.01)
  *H05H 1/24* (2006.01)
  *B08B 9/04* (2006.01)
  *C02F 1/78* (2006.01)
  *C02F 103/06* (2006.01)
  *C02F 103/00* (2006.01)
  *C02F 1/30* (2006.01)
  *C02F 1/72* (2006.01)
  *A61L 9/22* (2006.01)

(52) U.S. Cl.
  CPC .............. *C02F 1/78* (2013.01); *H05H 1/2406* (2013.01); *A61L 9/22* (2013.01); *A61L 2202/11* (2013.01); *A61L 2202/15* (2013.01); *A61L 2202/17* (2013.01); *A61L 2202/24* (2013.01); *A61L 2202/25* (2013.01); *C02F 1/30* (2013.01); *C02F 1/72* (2013.01); *C02F 2103/003* (2013.01); *C02F 2103/06* (2013.01); *C02F 2201/782* (2013.01); *C02F 2303/04* (2013.01); *C02F 2303/20* (2013.01); *C02F 2305/023* (2013.01); *C02F 2307/14* (2013.01); *H05H 1/2418* (2021.05); *H05H 1/2437* (2021.05); *H05H 1/2443* (2021.05)

(58) Field of Classification Search
  CPC . A61L 2202/17; A61L 2202/24; B08B 9/045; B08B 9/04; B08B 1/04; C02F 1/78; C02F 2303/20; C02F 2103/003; C02F 2103/06; C02F 2307/14; C02F 2201/782; C02F 2303/04; C02F 1/30; C02F 1/72; C02F 2305/023; H05H 1/2406; H05H 2001/2437; H05H 2001/2443
  See application file for complete search history.

(56) References Cited

U.S. PATENT DOCUMENTS

| | | | |
|---|---|---|---|
| 6,695,664 B2 | 2/2004 | Eden et al. | |
| 6,815,891 B2 | 11/2004 | Eden et al. | |
| 6,867,548 B2 | 3/2005 | Eden et al. | |
| 7,477,017 B2 | 1/2009 | Eden et al. | |
| 7,482,750 B2 | 1/2009 | Eden et al. | |
| 7,573,202 B2 | 8/2009 | Eden et al. | |
| 7,615,926 B2 | 11/2009 | Eden et al. | |
| 7,638,937 B2 | 12/2009 | Eden et al. | |
| 8,004,017 B2 | 8/2011 | Eden et al. | |
| 8,159,134 B2 | 4/2012 | Eden et al. | |
| 8,179,032 B2 | 5/2012 | Eden et al. | |
| 8,221,179 B2 | 7/2012 | Eden et al. | |
| 8,404,558 B2 | 3/2013 | Eden et al. | |
| 8,442,091 B2 | 5/2013 | Park et al. | |
| 8,497,631 B2 | 7/2013 | Eden et al. | |
| 8,535,110 B2 | 9/2013 | Eden et al. | |
| 8,547,004 B2 | 10/2013 | Eden et al. | |
| 8,864,542 B2 | 10/2014 | Eden et al. | |
| 8,870,618 B2 | 10/2014 | Eden et al. | |
| 8,890,409 B2 | 11/2014 | Eden et al. | |
| 8,957,572 B2 | 2/2015 | Eden et al. | |
| 8,968,668 B2 | 3/2015 | Eden et al. | |
| 9,390,894 B2 | 7/2016 | Eden et al. | |
| 2005/0206290 A1 | 9/2005 | Kunhardt et al. | |
| 2007/0200499 A1* | 8/2007 | Eden ................... H01J 65/046 | 313/582 |
| 2009/0121638 A1 | 5/2009 | Price et al. | |
| 2015/0270110 A1* | 9/2015 | Eden ................. H01J 37/32798 | 422/186.04 |

OTHER PUBLICATIONS

Bridier et al., "Resistance of bacterial biofilms to disinfectants: a review", Biofouling, vol. 27, No. 9, pp. 1017-1032, Oct. 2011.

Kolb et al., "Cold Atmospheric Pressure Air Plasma Jet for Medical Applications", Applied Physics Letters, vol. 92, 241501, Jun. 17, 2008.

Lau et al., "The role of biofilms and protozoa in Legionella pathogenesis: implications for drinking water", Journal of Applied Microbiology, vol. 107, pp. 368-378, 2009.

Li et al., "A brush-shaped air plasma jet operated in glow discharge mode at atmospheric pressure", Journal of Applied Physics, vol. 116, 023302, 2014.

Liu et al., "A study of the glow discharge characteristics of contact electrodes at atmospheric pressure in air", Physics of Plasmas, vol. 21, 043514, 2014.

Won et al., "Ozone-Free Portable Microwave Atmospheric Air Plasma Jet", IEEE Transactions On Plasma Science, vol. 42, No. 10, Oct. 2014.

* cited by examiner

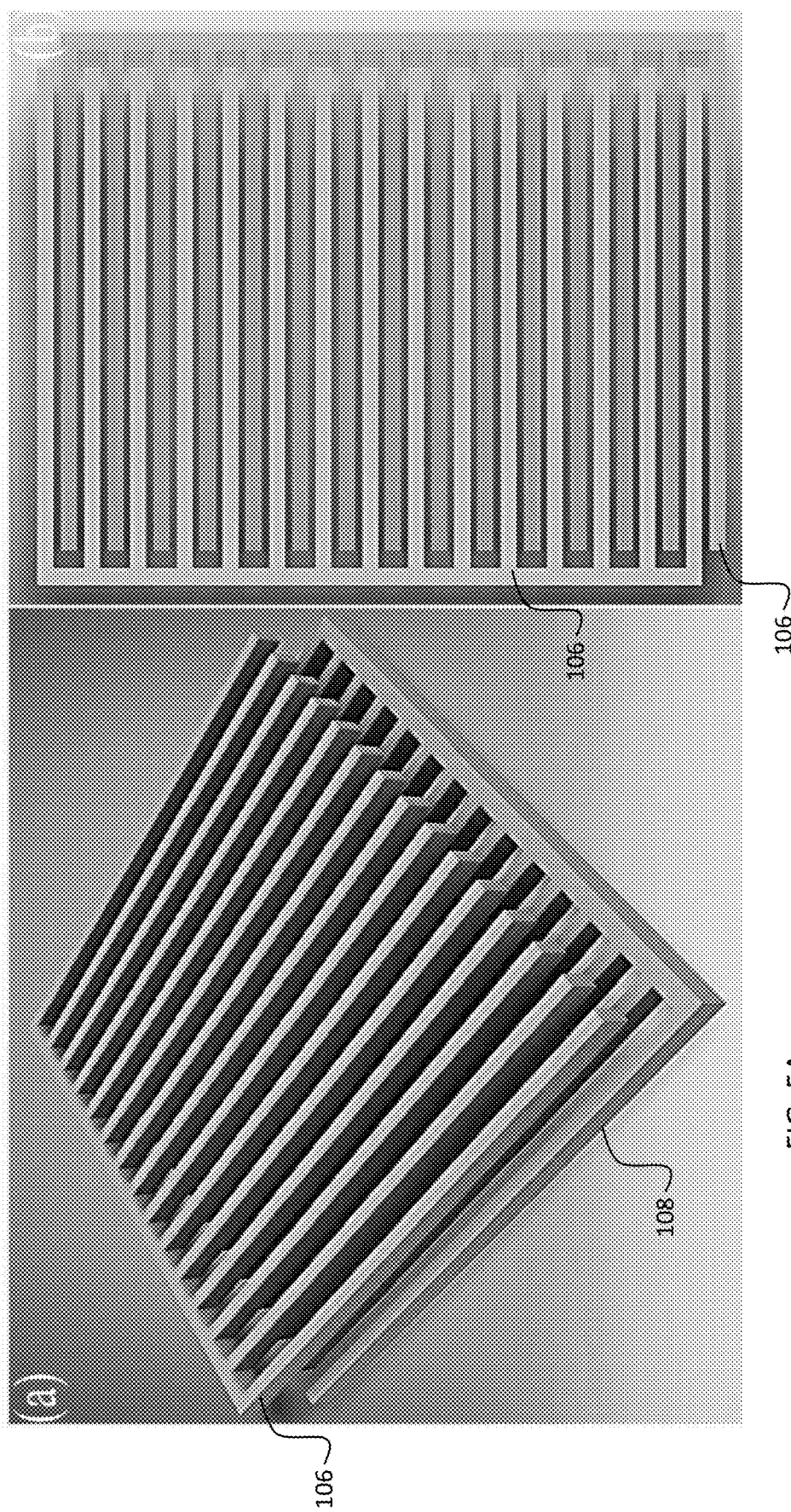

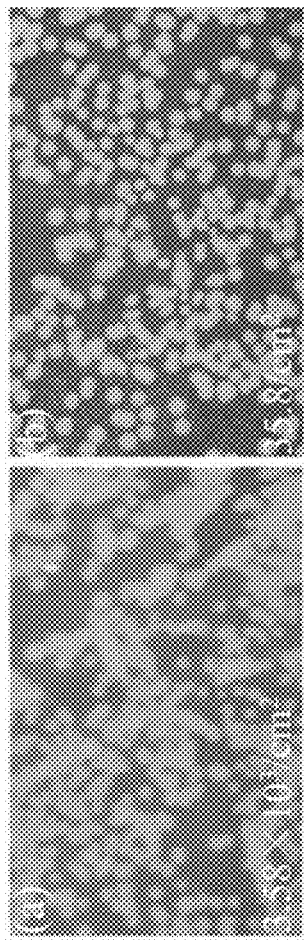
FIG. 7A
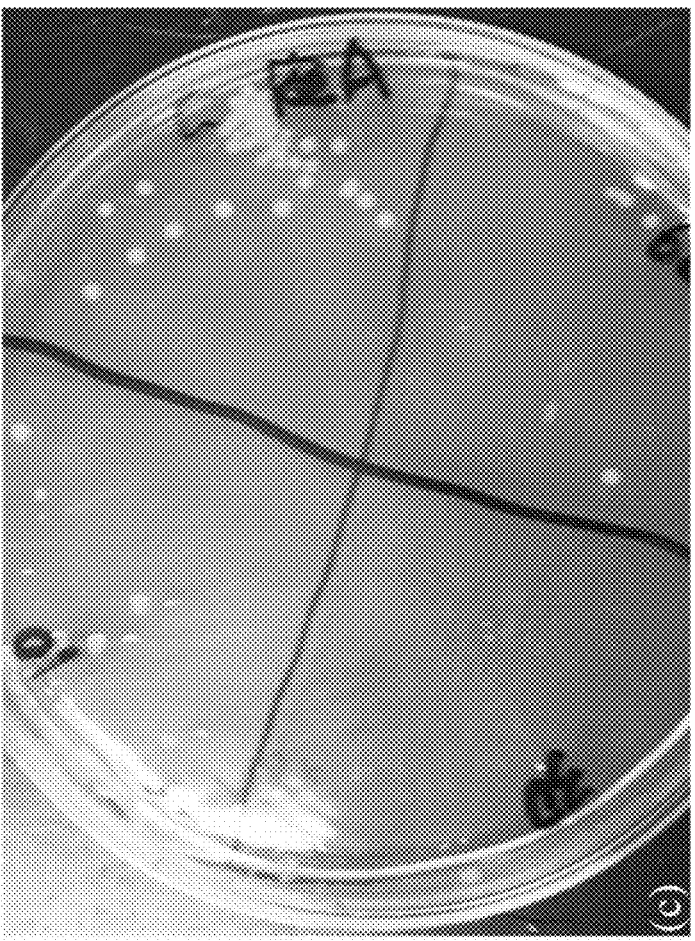
FIG. 7B
FIG. 7C

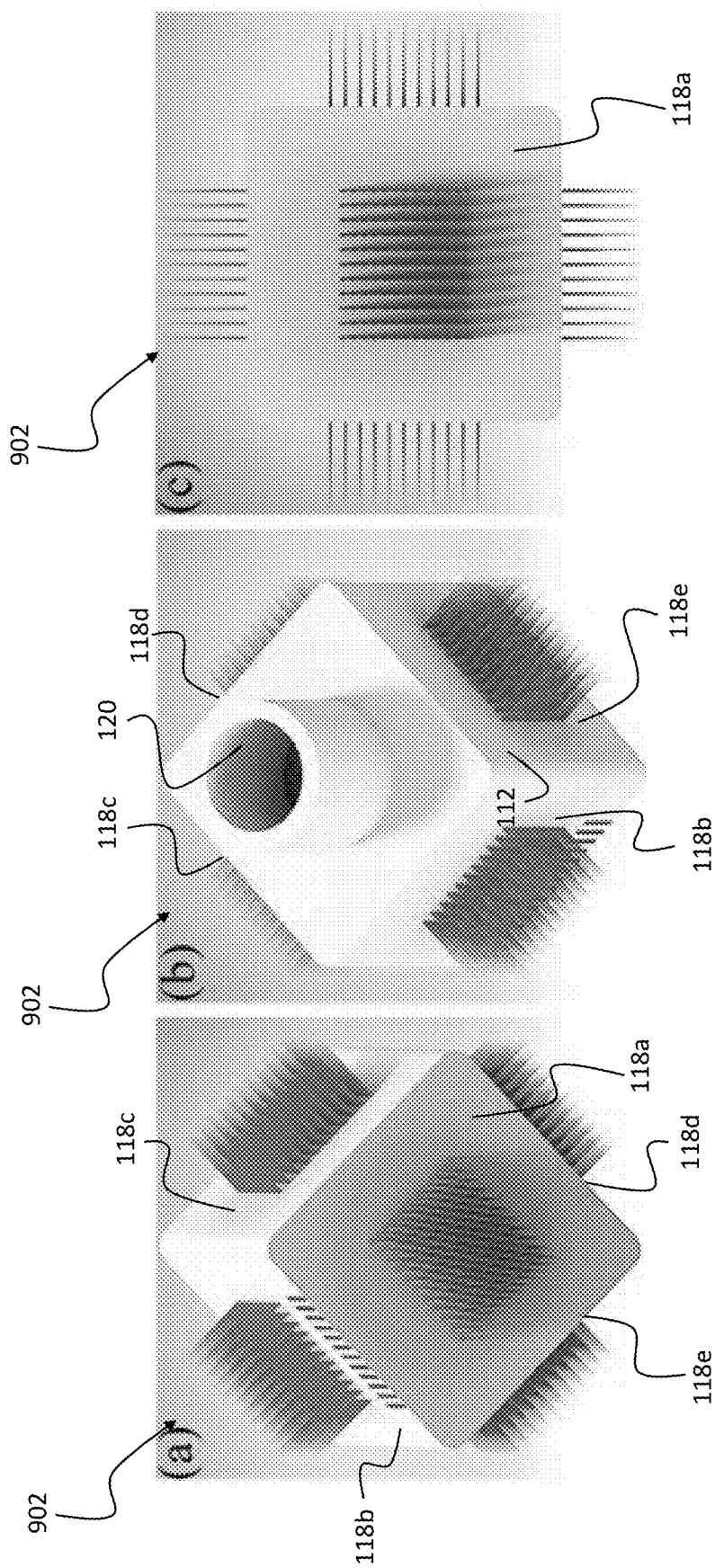

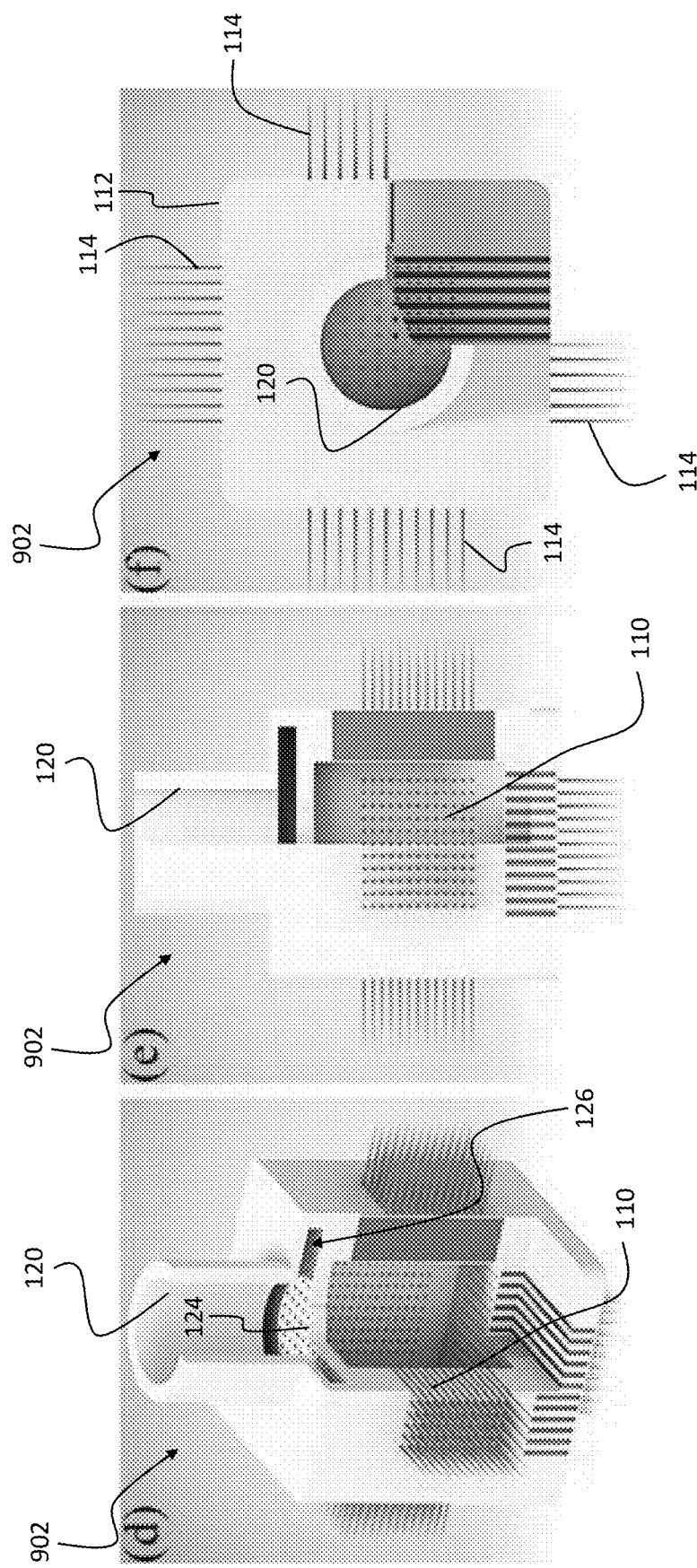

MICROPLASMA DEVICES FOR SURFACE OR OBJECT TREATMENT AND BIOFILM REMOVAL

PRIORITY CLAIM AND REFERENCE TO RELATED APPLICATION

The application claims priority under 35 U.S.C. § 119 and all applicable statutes and treaties from prior U.S. provisional application Ser. No. 62/508,389, which was filed May 18, 2017.

STATEMENT OF GOVERNMENT INTEREST

This invention was made with government support under contract no. FA9550-14-1-0002 awarded by the U.S. Air Force Office of Scientific Research. The government has certain rights in the invention.

FIELD

Fields of the invention include microchannel plasma devices (also known as microplasma devices), microplasma jet arrays, surface, air, and water disinfection, biofilm removal, and hospital acquired infection prevention.

BACKGROUND

Hospital-acquired infections (HAIs) are an epidemic that threatens patients, treatment clinics, hospitals and the entire health care system. Tens of thousands of Americans (and many others worldwide) die annually from hospital-acquired infections (HAIs) acquired by exposure of the patient at a health care facility. Infected surfaces, such as those associated with bed linens, tables, chairs, railings, sinks, faucets, as well as medical instrumentation and supplies, often harbor pathogens that lead to infections. Standard and enhanced cleaning procedures used in hospitals, most of which are based on liquid disinfectants, have proven insufficient to combat the growing threat. A recent study conducted at the University of Virginia (published in *Applied and Environmental Microbiology*, 2017) has demonstrated that pathogens grow and multiply in the trap located beneath all sinks. They subsequently produce a biofilm that grows up the faucet pipe to the sink drain. The final step is the airborne dispersion of pathogens entrained in the mist (small water droplets) produced when the water stream from the faucet strikes the drain. The Virginia study showed that the mist is capable of transporting pathogens up to 0.75 meters from the drain. The mist can either be directly ingested by the patient, or the pathogens can be propagated when the patient or others touches a nearby surface.

Another infection problem of growing concern is related to the long-known existence of biofilms in municipal, commercial, and residential water systems. Biofilms are ubiquitous and it has long been known that they thrive in water systems. While many films are harmless, biofilms are also capable of harboring a variety of serious pathogens, such as *Legionella pneumophila*. Water companies generally attempt to compensate for the gradual buildup of biofilms on the interior surfaces of water pipes by increasing the concentration of chlorine introduced to the water. Unfortunately, some biofilms are virtually impervious to chlorine or other disinfectants. Furthermore, biofilms have been shown to capture and accumulate planktonic pathogens and subsequently release these species into air or a water flow stream by the detachment of biofilm material. See, Lau, H. Y.; Ashbolt, N. J., "The Role of Biofilms and Protozoa in *Legionella* Pathogenesis: Implications for Drinking Water," *J. Appl. Microbiol.* 2009, 107 (2), 368-378. Although residual disinfectants in drinking water are mandated by the U.S. Environmental Protection Agency (EPA) for microorganism control in drinking water distribution systems, biofilms persist despite exposure to disinfectants because the extracellular polymeric substance produced by biofilms consumes the disinfectant, thereby hindering or preventing disinfectant permeation. See, Kim, B. R.; Anderson, J. E.; Mueller, S. A.; Gaines, W. A.; Kendall, A. M., "Literature Review—Efficacy of Various Disinfectants against *Legionella* in Water Systems," *Water Res.* 2002, 36 (18), 4433-4444; Bridier, A.; Briandet, R.; Thomas, V.; Dubois-Brissonnet, F., "Resistance of Bacterial Biofilms to Disinfectants: A Review," *Biofouling* 2011, 27 (9), 1017-1032.

The present inventors and colleagues have developed and patented a number of microcavity and microchannel plasma devices. Examples of such microcavity and microchannel plasma devices are found in the following U.S. Patents:

| | |
|---|---|
| 9,390,894 | Modular Microplasma MicroChannel Reactor Devices, Miniature Reactor Modules and Ozone Generation Devices. |
| 8,968,668 | Arrays of Metal and Metal Oxide Microplasma Devices With Defect Free Oxide |
| 8,957,572 | Microplasma Jet Devices, Arrays, Medical Devices and Methods |
| 8,890,409 | Microcavity and MicroChannel Plasma Device Arrays in a Single, Unitary Sheet |
| 8,870,618 | Encapsulated Metal Microtip Microplasma Device and Array Fabrication Methods |
| 8,864,542 | Polymer Microcavity and MicroChannel Device and Array Fabrication Method |
| 8,547,004 | Encapsulated Metal Microtip Microplasma Devices, Arrays and Fabrication Methods |
| 8,535,110 | Method to Manufacture Reduced Mechanical Stress Electrodes and Microcavity Plasma Device Arrays |
| 8,497,631 | Polymer Microcavity and MicroChannel Devices and Fabrication Method |
| 8,442,091 | MicroChannel Laser Having Microplasma Gain Media |
| 8,404,558 | Method For Making Buried Circumferential Electrode Microcavity Plasma Device Arrays, and Electrical Interconnects |
| 8,221,179 | Method of Making Arrays of Thin Sheet Microdischarge Devices |
| 8,179,032 | Ellipsoidal Microcavity Plasma Devices and Powder Blasting Formation |
| 8,159,134 | Arrays of Microcavity Plasma Devices and Electrodes With Reduced Mechanical Stress |
| 8,004,017 | Buried Circumferential Electrode Microcavity Plasma Device Arrays, Electrical Interconnects, and Formation Method |
| 7,638,937 | Roll to Roll Method of Making Microdischarge Devices and Arrays |
| 7,615,926 | Low Voltage Microcavity Plasma Device and Addressable Arrays |
| 7,573,202 | Metal/Dielectric Multilayer Microdischarge Devices and Arrays |
| 7,482,750 | Plasma Extraction Microcavity Plasma Device and Method |
| 7,477,017 | AC-Excited Microcavity Discharge Device and Method |
| 6,867,548 | Microdischarge Devices and Arrays |
| 6,815,891 | Method and Apparatus For Exciting a Microdischarge |
| 6,695,664 | Microdischarge Devices and Arrays |
| 6,563,257 | Multilayer Ceramic Microdischarge Device |

The plasma arrays described in the '572 patent produce jets that can be applied to human skin for the purpose of disinfection and the acceleration of wound healing, and to surface treatment of inorganic materials. The jet arrays were formed in a monolithic block of polymer. The arrays in the '572 patent require the flow of a plasma medium (feedstock gas) which can consist of one or more noble gases (He, Ne, Ar, Kr, or Xe) and mixtures with nitrogen, oxygen, air and/or hydrogen. The jets produced extend a short distance outside of the array, up to several centimeters. It should be noted that the production of these jets requires a high-pressure gas cylinder, or other feedstock gas source, to be attached to the micron gay. Furthermore, the primary material used in these systems (polydimethysiloxane: PDMS) as the housing for the plasma channel array is not compatible with an electrical discharge in air because of its dielectric breakdown strength (air requires a breakdown strength as least 3 kV/mm) Furthermore, several species generated in plasmas generated from air (such as ozone) will degrade polymers such as PDMS and limit the lifetime of the jet array. In short, the plasma arrays of the '572 patent are incompatible with the production of microplasma arrays when room air is the feedstock gas.

The reactors in the '894 patent are capable of producing ozone for the disinfection of water, food products, laundry, surfaces, wounds, and medical instruments, for example. The reactor devices and systems employ air or oxygen as the "feedstock" gas to generate ozone efficiently. In one embodiment, a sprayer plate serves to distribute ozone. A reactor with such a sprayer plate can be deployed, for example, in a food package. Another embodiment uses a fan and a sprayer/disperser. These reactors do not produce jets in the manner of the '572 patent, but rather produce a desired plasmachemical product internal to the microchannel arrays.

Additional background information can be found in the following patent documents and publications.

PATENT DOCUMENTS

US 20090121638 to Price et al. Cold air atmospheric pressure micro plasma jet application method and device.
U.S. Pat. No. 5,876,663 Mounir Laroussi, Sterilization of liquids using plasma glow discharge,
US 20050206290 Kunhardt & Becker, Method and apparatus for stabilizing of the glow plasma discharges.

PUBLICATIONS

J. Kolb, A. Mohamed, R. Price, R. Swanson, A. Bowman, R. Chiavarini, M. Stacey, and K. Schoenbach, "Cold atmospheric pressure air plasma jet for medical applications," Appl. Phys. Lett., 92, 241501, 2008.
I. H. Won, S. K. Kang, J.-Y. Sim, and J. K. Lee, "Ozone-Free Portable Microwave Atmospheric Air Plasma Jet," IEEE Trans. Plasma Sci., 42, 2788, 2014.
X. Li, W. Bao, P. Jia, and C. Di, "A brush-shaped air plasma jet operated in glow discharge mode at atmospheric pressure," J. Appl. Phys, 116, 023302, 2014.
W. Liu, G. Sun, C. Li, and R. Zhang, "A study of the glow discharge characteristics of contact electrodes at atmospheric pressure in air," Phys. Plasmas, 21, 043514, 2014.

SUMMARY OF THE INVENTION

A preferred embodiment provides an array of elongate microchannels formed in a polymer or ceramic housing having tolerance to ozone and other radicals formed when plasma is generated from air in the microchannels. The microchannels include inlets configured to accept an air feed, and outlets configured to direct plasma jets toward a surface (which may be the internal surface of a pipe, for example) or object. An array of electrodes within the housing is configured to ignite and maintain plasma in the microchannels and is isolated by the housing from the microchannels. A supply intake is configured for providing a plasma medium into the microchannels. The housing is preferably fabricated from a polymer such as an ABS or ABS-like plastic. The device can be configured in a variety of physical configurations, such as cubes or tubes. Jets can extend from multiple surfaces, or radially. Municipal water supply disinfection device configurations are provided, as well as configurations for water drain and supply pipes. Microplasma arrays of the invention are capable of producing jets that extend from the array to treat surfaces or other objects (such as medical instruments) and can be fed solely by room air.

BRIEF DESCRIPTION OF THE DRAWINGS

FIGS. 5A-5B illustrate the electrode arrays for the exemplary embodiment of FIGS. 4A-4D;

FIGS. 7A-7C are images illustrating the results of experiments in which E. coli bacteria have been deactivated through exposure to experimental arrays of the invention;

FIGS. 9A-9F illustrate a preferred device of the invention that provides microplasma jets emerging from a plurality of surfaces;

DETAILED DESCRIPTION OF THE PREFERRED EMBODIMENTS

Figure 1C:
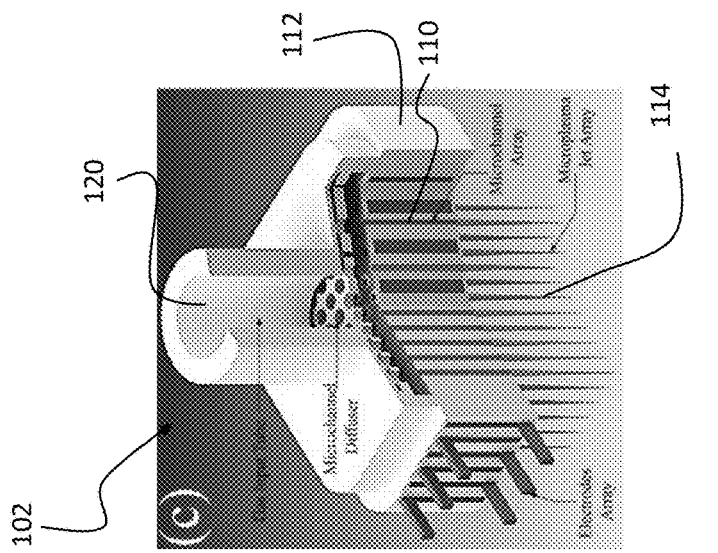
FIGS. 1A-1C illustrate a preferred air fed microplasma device of the invention that generates an electric field oriented along a coordinate perpendicular to the microchannels.

Preferred embodiments of the invention provide arrays of microplasma jets that are ideally suited for disinfecting surfaces, and deactivating biofilms and the pathogens they harbor. Microplasma arrays of the invention are capable of producing jets that extend from the array to treat surfaces or other objects (such as medical instruments) but, unlike the '572 patent, can be fed solely by room air which serves as the feedstock gas for the array. No other source of gas is required, thereby reducing dramatically the cost and size of the system, as compared to the devices of the '572 patent. Preferred arrays provide the ability to generate spatially uniform plasmas directly in air, which results in the production of molecular radicals (such as the hydroxyl radical, OH) known to be lethal to micro-organisms such as *E. coli* and *Giardia*. In preferred embodiments, the effective range of the microplasma array (i.e., distance over which the microplasmas are effective in bringing about disinfection) generally extends well beyond the physical dimensions of the visible plasma, because it is the radicals and excited atoms and molecules produced by the plasma that are primarily responsible for deactivating pathogens. The range of these species (distance traveled before they are deactivated) is dependent on their lifetimes which can be as large as milliseconds and can approach one second. Such lifetimes translate into distances traveled as large as several meters at room temperature and pressure.

Preferred arrays of the invention are formed via three-dimensional (3D) printing processes in plastic-like material (such as ABS (Acrylonitrile butadiene styrene) or ABS-like material) that can tolerate the high electric fields necessary for generating plasma from an air feedstock. ABS-like material is produced from a low viscosity liquid photopolymer that yields strong, tough, water-resistant structures and yet mimics traditional engineering plastics, including ABS and PBT (Polybutylene terephthalate). These properties make the material ideal for many applications in the automotive, medical and consumer electronic markets. Representative products produced from this material include lenses, packaging, water flow analysis, RTV (room temperature vulcanization) patterns, durable concept models, wind tunnel testing and investment casting patterns. Surprisingly, however, these materials were also found to withstand the plasma, radicals and electrical fields encountered in preferred devices. The dimensions of the electrodes, lengths of channels, spacing of electrodes and power supplied to the system are able to produce electric field strengths (expressed in kV/mm) that meet and exceed the level required to guarantee plasma jet generation from the air used as a plasma medium (feedstock gas). Preferred arrays can generate and tolerate high electric fields of at least 3 kV/mm, preferably well in excess of 8 kV/mm, and generally in the range of 4 kV/mm to 25 kV/mm. The field strength required for a particular plasma array will depend upon the particular polymer, plastic-like material, or ceramic used. Preferred materials such as ABS tolerate a preferred field strength between 6 kV/mm and 16 kV/mm. The key characteristics of the material chosen include that the ability to be compatible with 3D printing and, as discussed above, to tolerate the desired electric field strengths.

Figure 1B:
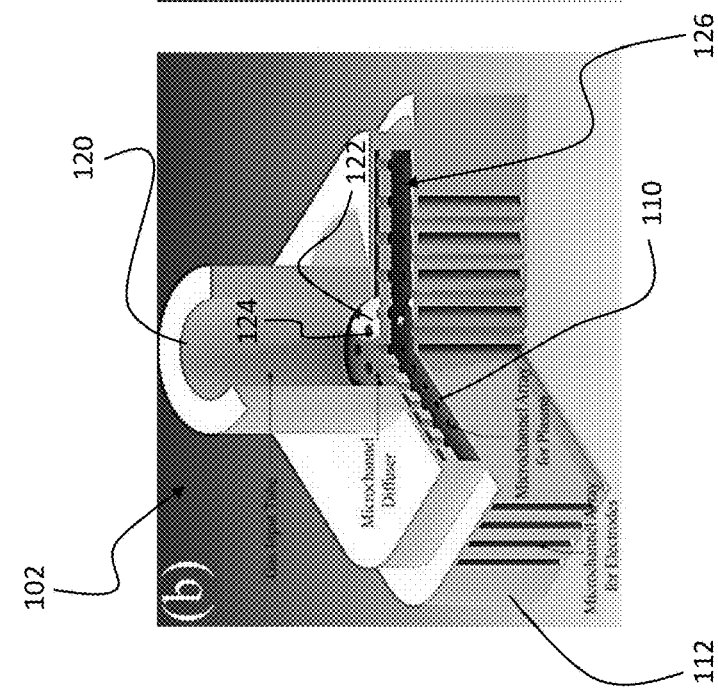
Figure 1A:
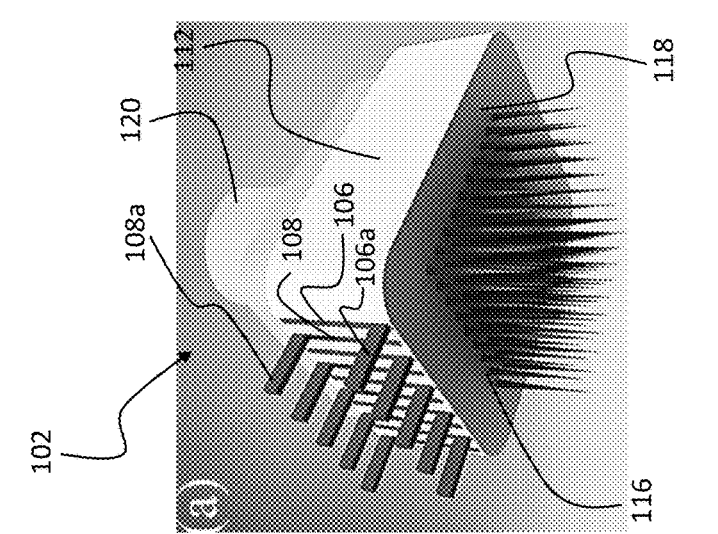
Figure 1F:
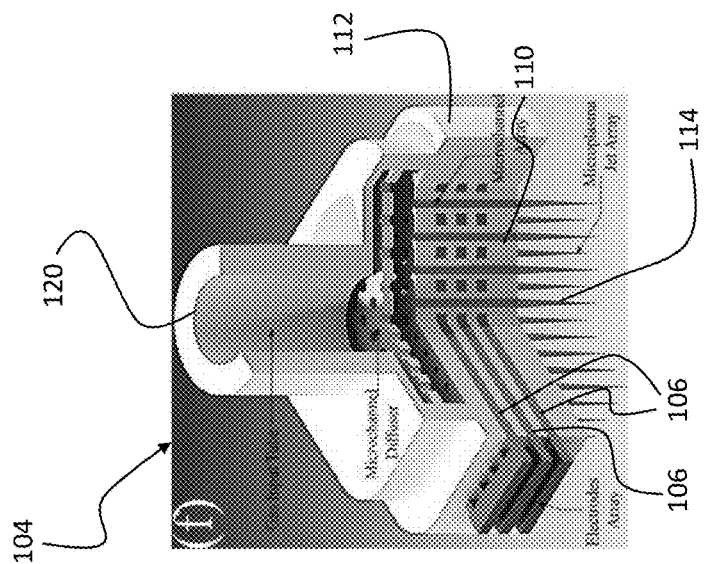
FIGS. 1D-1F are diagrams of a preferred air-fed microplasma device of the invention that generates an electric field oriented parallel to the microchannels.
Figure 1E:
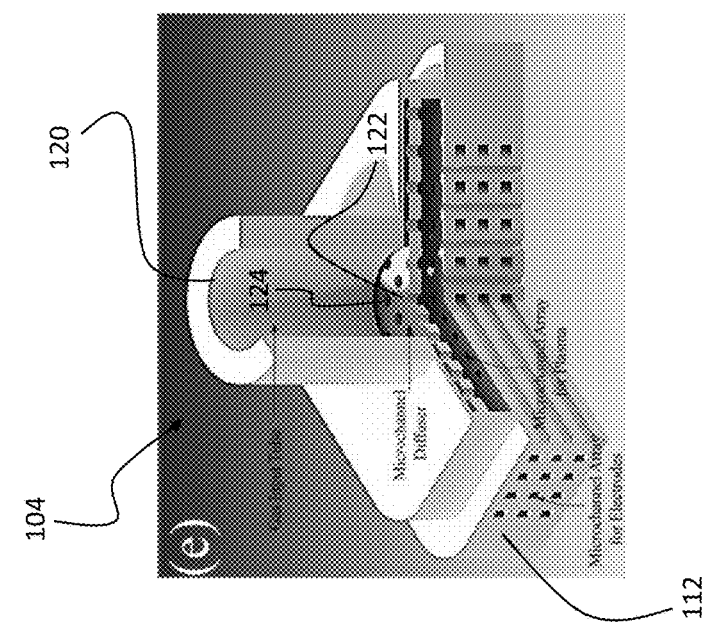
Figure 1D:
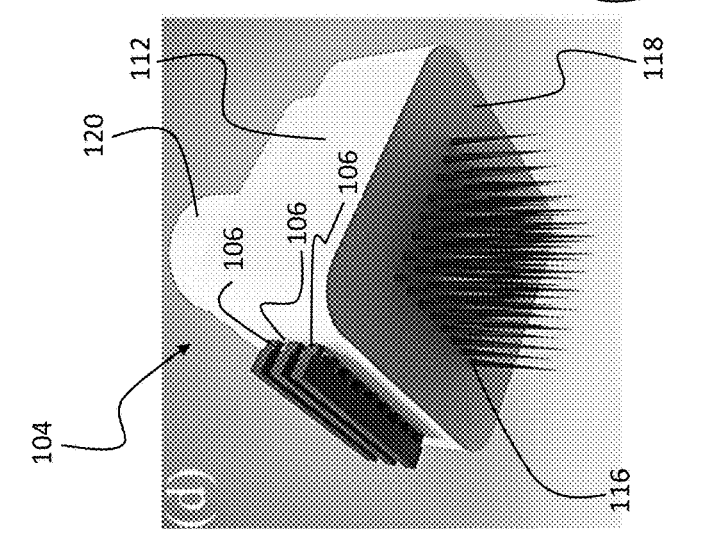

FIGS. 1A-1C illustrate a preferred air fed microplasma array device 102 of the invention in which the orientation of the electric field is orthogonal to the air flow direction, and FIGS. 1D-1F illustrate a preferred air-fed microplasma array device 104 of the invention in which the orientation of the electric field is parallel to the direction of air flow. The relative arrangement of electrode array pairs 106, 108 in the microplasma arrays determines the orientation of the electric field, but the arrays 102 and 104 otherwise include common features, which are labelled with common reference numerals. In FIGS. 1A-1C, electrode arrays 106 and 108 are arranged parallel to the longitudinal axes of, and disposed around, individual ones of an array of microchannels 110 so as to generate a transverse electric field when powered by a time-varying voltage imposed on the electrode arrays 106 and 108. In FIGS. 1D-1F, electrode arrays 106 and 108 are arranged so as to be perpendicular to the longitudinal axes of, and disposed between, individual ones of an array of microchannels 110 so as to generate an electric field parallel to the gas flow when powered by a time-varying voltage across the electrode arrays 106 and 108. As one side of the device 104 is hidden in FIGS. 1D-1F, only the array 106 is visible in FIGS. 1D-1F, but electrode array 108 is shown in FIGS. 5A and 5B. FIGS. 1D-1F also show three arrays 106 (and implies the presence of the three arrays 108), which tend to extend a uniform electrode field as compared to a single electrode array 106 with a single array 108. However, only a single electrode array 106 with a single array 108 is required. Alternatively, a single electrode array 106 in which individual "fingers" are isolated from each other and are separately powered to create the required electric field across individual microchannels can also be used. External contacts 106a and 108a are shown extending from the electrodes 106 and 108 in FIGS. 1A-1C, but electrodes 106 and 108 can also be directly powered by a time-varying voltage source. The microchannels 110 and spaces for the electrodes 106 and 108 in the devices 102 and 104 are fabricated in a monolithic block 112 of dielectric material. The monolithic block 112 is preferably formed of 3D printable material that is able to tolerate the high electric field strengths necessary to generate plasma jets 114 extending from exit ports 116 of the microchannels 110 when room air is the feedstock gas. The exit ports 116 are defined by the intersections of the microchannels 110 at an outer surface 118 of the monolithic block 112.

Figure 1G:
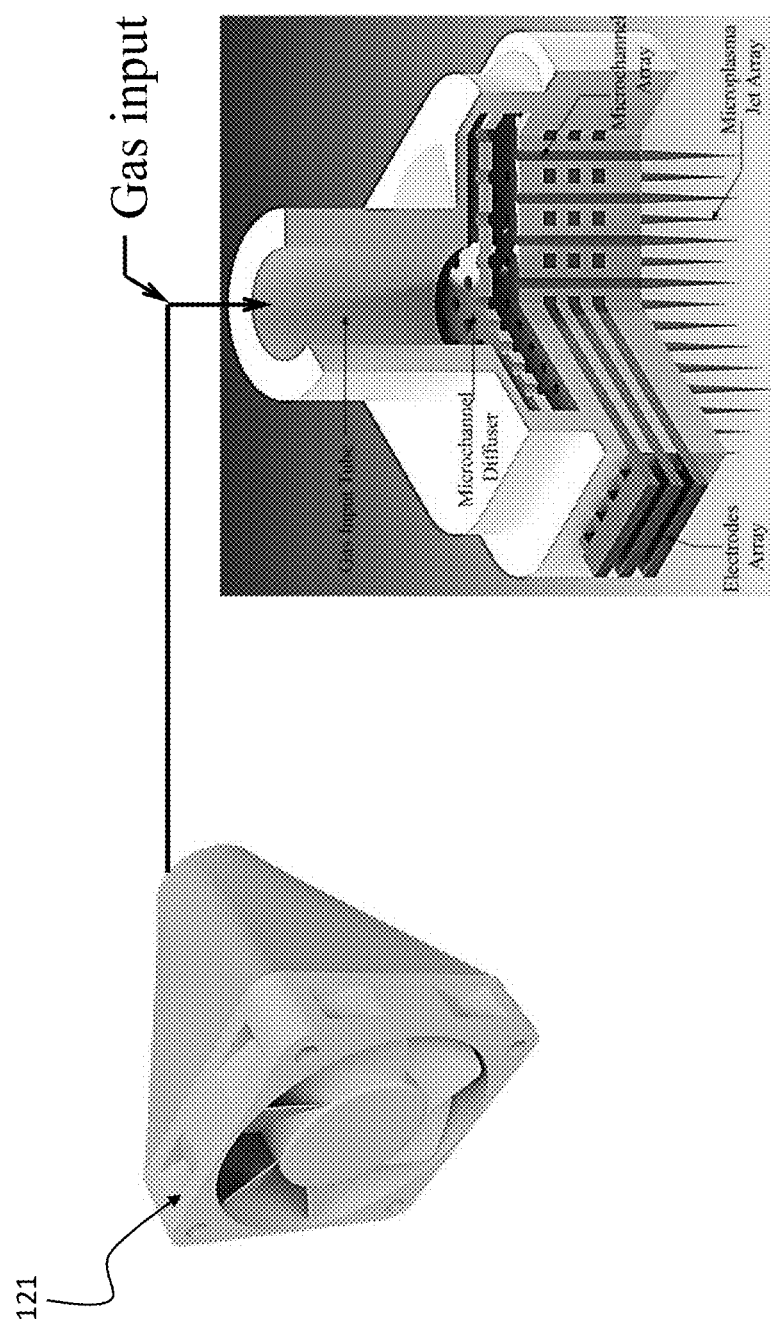
FIG. 1G shows a fan and compressor for the air fed microplasma device.

The cutaway view of FIGS. 1B and 1E illustrates the cross-section of the devices 102, 104 in the absence of the electrodes 106 and 108. An air supply intake feed 120 is in the form of a cylindrical gas entry tube having a diameter of several mm (typically, 5-7 mm) The feed 120 supplies air to a diffuser 122, which has the purpose of apportioning the incoming gas equally among the microchannels and minimizing turbulence. The diffuser includes a plurality of microchannels 124. The diffuser 122 defines, and is separated from, inlets of the microchannels 110 by a volume 126. The diffuser 122 can be monolithically formed with the monolithic block structure 112, or can be formed separately and then attached. Example diameters for the microchannels 124 of the diffuser range from 50 µm to a few millimeters. Experiments have shown the diffuser 122 with microchannels 124 to have a pronounced positive influence on the uniformity of all of the plasma jets in an array. The length of microchannels 124 in the diffuser 122 in experimental devices was 2-10 mm. For a particular design, the diffuser dimensions can be optimized to uniform flow of air or another plasma medium to the microchannels 110. When a time-varying voltage is supplied to the device, plasmas are generated in each microchannel 110, and the plasmas emerge as jets 114. The jets extend as much as several mm from outer surface 118 but the beneficial impact of the plasma arrays extends much further than the visible length of the plasmas. The primary function of the microplasmas is to generate, either in the microplasmas themselves or through the interaction of the individual plasmas with the ambient gas (or gases), atomic and molecular excited species having internal energies of several eV or more and lifetimes in air that are sufficient to allow these species to travel to a surface or another object. It is the interaction of these excited species (or radicals in their ground state) that appears to be responsible for deactivating pathogens and thinning or removing biofilms. Furthermore, the characteristics of the microplasmas in devices 102 and 104 are different from each other because plasma characteristics are altered when the orientation of the electric field that ignites and maintains plasma is changed. This distinction is of value in producing different atomic or molecular species (when desired) in the plasma jets. Advantageously, either of the devices 102 and 104 can use air as a plasma medium. In order to provide an adequate flow of air through the microplasma array (generally, at least 0.5 standard liters per minute (slm)), it is often desirable to insert a small fan and/or air compressor 121 (FIG. 1G, within the feed 120) into the flow line "upstream" of the microplasma array. The array, of course, can also generate plasma jets with other plasma media, e.g. the noble gases and mixtures of noble gases, noble gases with oxygen or nitrogen, etc. However, a great advantage of the invention is that the material(s) from which the array is fabricated tolerates (i.e., is resistant to erosion by) the radicals and excited species generated with air as a plasma medium, and is more resistant to dielectric breakdown than is, for example, PDMS. Perhaps most importantly, the jet arrays described here do not require the gas supply of the '572 patent because ambient (room) air can serve as the medium for the plasma. Consequently, the cost of the array devices is reduced, and the mobility and utility of the technology are greatly enhanced.

Figures 2A, 2B, 2C, 2D:
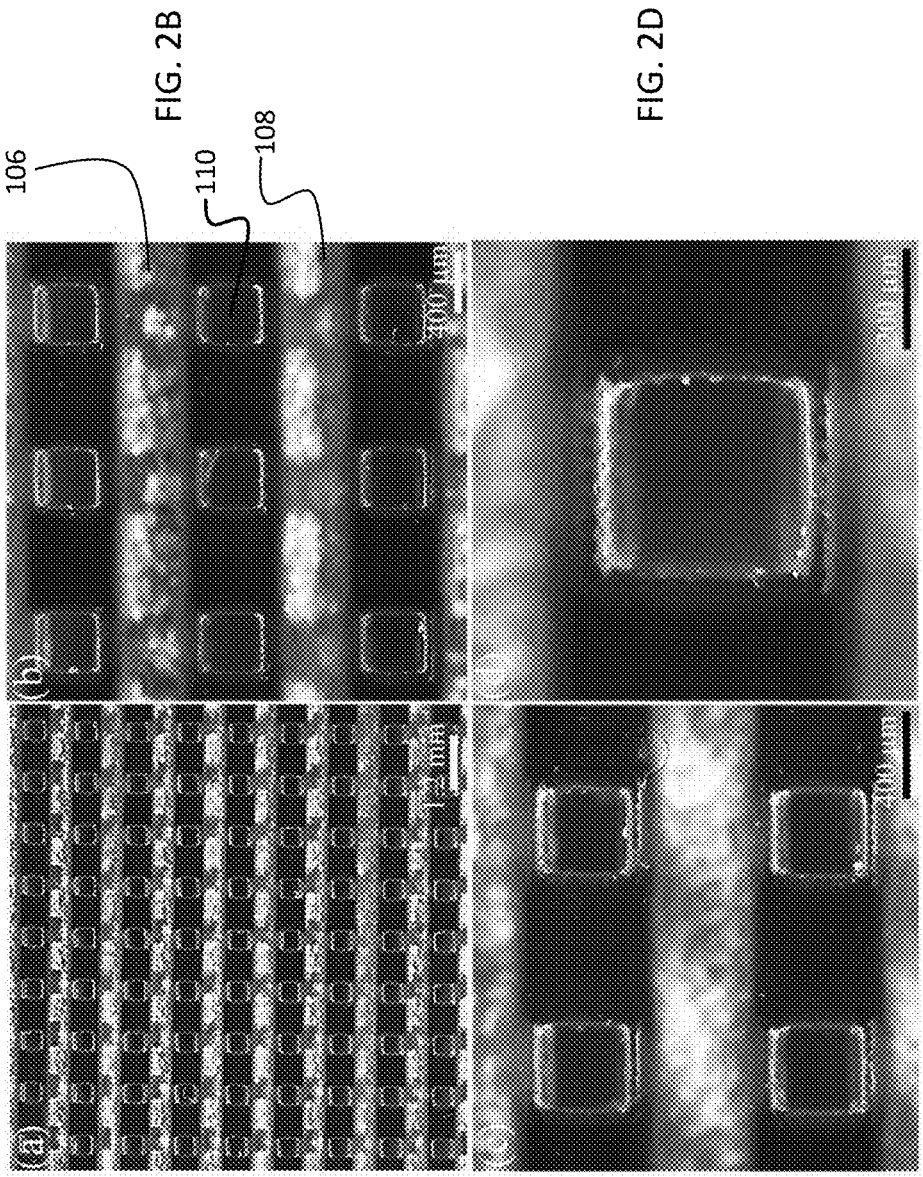
FIGS. 2A-2D are bottom view optical micrographs at different magnifications of an experimental device consistent with FIGS. 1D-1F.

FIGS. 2A-2D are micrographs of a cross-section of an experimental device. The example experimental devices have microchannels 110 that are approximately square in cross-section. Each microchannel has a 400×400 μm² square cross-section, and the images show one or more microchannels and their associated electrodes at successively greater levels of magnification. A 9×9 array of microchannels, having an overall area of 125.4 mm² (1.25 cm²) is presented in FIG. 2A, whereas only a single microchannel from the array is shown FIG. 2D. The pitch (center-to-center spacing) between adjacent channels is 1.2 mm along both the horizontal and vertical axes of the two-dimensional array which defines the areal packing density of the array as 88 channels/cm². Experimental arrays were fabricated with a 3D printing tool having a spatial resolution of 50 μm. FIG. 2D shows that, aside from a slight "bowing" of the sidewalls of the channels, this limitation in the tool resolution has no significant adverse consequences. The images show that portions of the dielectric monolithic structure both separate and insulate the microchannels from the electrodes.

Figure 3B:
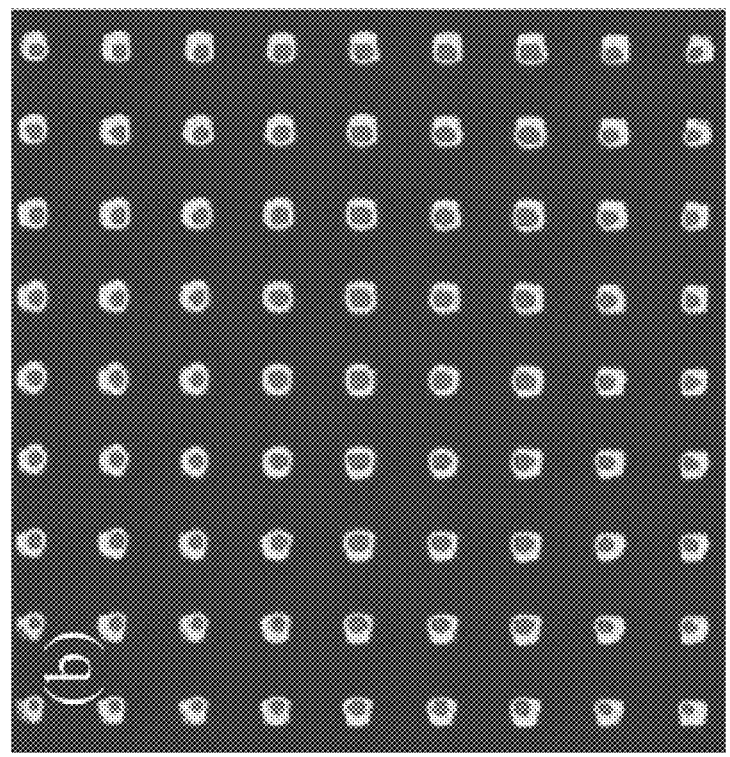
FIGS. 3A (regular) & 3B (false color) present time-integrated images from an example experimental device operating with He and the feedstock gas.
FIG. 3C is a plot of the relative intensity at positions within and extending from the microchannels.
Figure 3A:
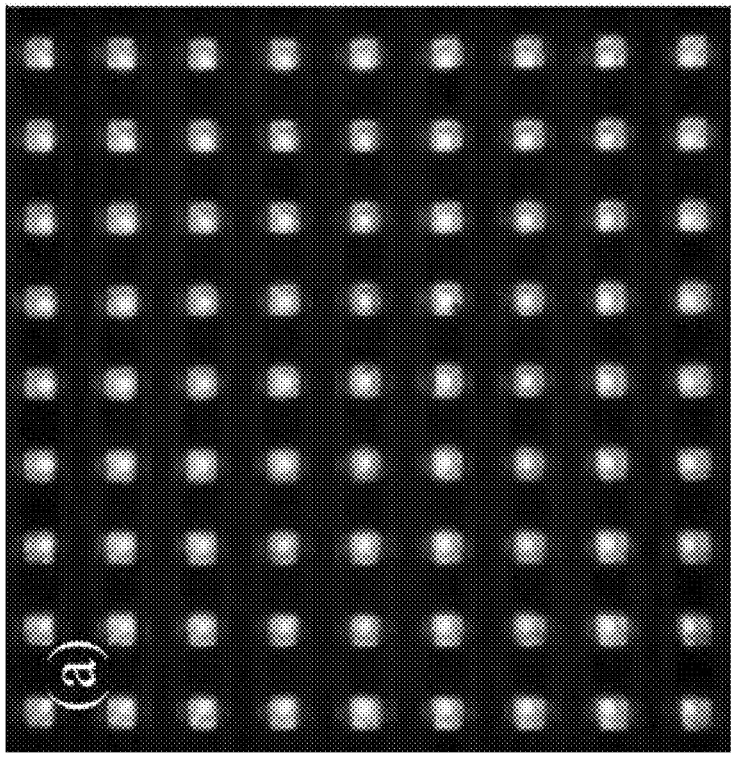
Figure 3C:
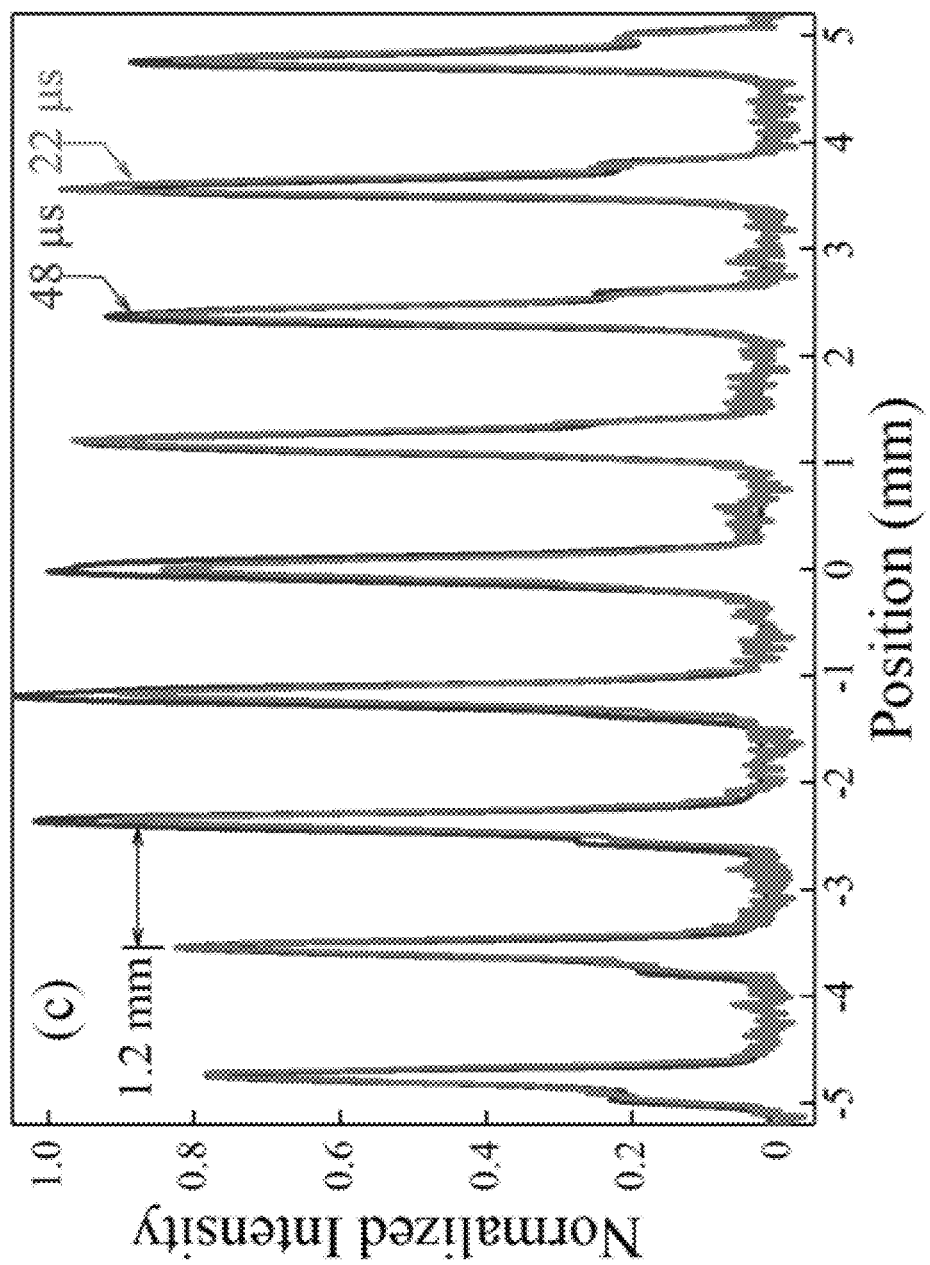

FIGS. 3A-3B present time-integrated images from an example experimental device operating in He, and FIG. 3C is a plot of intensity at positions within and extending from the microchannels. FIG. 3A is an end-on view of the fluorescence generated when the array is driven by a 20 kHz sinusoidal voltage waveform having an RMS value of 1.2 kV. Integrated over a 50 μs window (a full cycle of the driving voltage), the intensified charge-coupled device (ICCD) camera image FIG. 3A demonstrates that spatially uniform glow plasmas are produced within the square microchannels, but the most intense emission emanates from a cylindrical region having a diameter of 200-300 μm. Images similar to that of FIG. 3A were recorded for power densities of 3.6-79 W/cm² dissipated by the array. FIG. 3B is a false color image of the intensity map (derived from images such as that in FIG. 3A) acquired for a power density of 58 W/cm², and demonstrates the uniformity of the peak emission over the entire array. Two intensity lineouts of the central column of microchannel plasmas (FIG. 3C) shows that the difference between the integrated intensity produced by the interior channels differs by less than 25% from that emanating from the channels at the perimeter of the array. The lineouts of FIG. 3C were derived from images recorded over a 500 ns interval centered at t=22 μs or t=48 μs after the zero-crossing for the positive half-cycle of the 20 kHz voltage waveform.

Figure 4B:
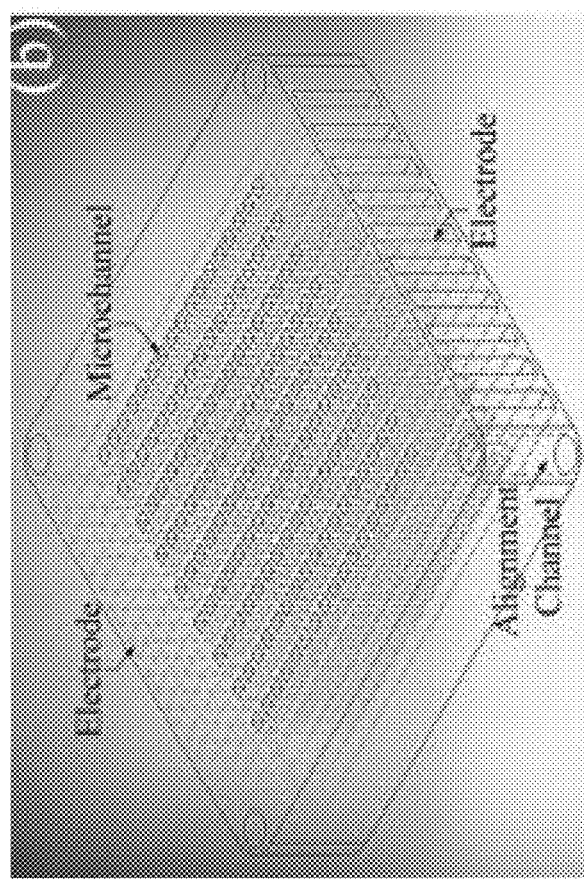
FIGS. 4A-4D present several views, and the dimensions, of an experimental device of the invention consistent with the embodiment of FIGS. 1D-1F.
Figure 4A:
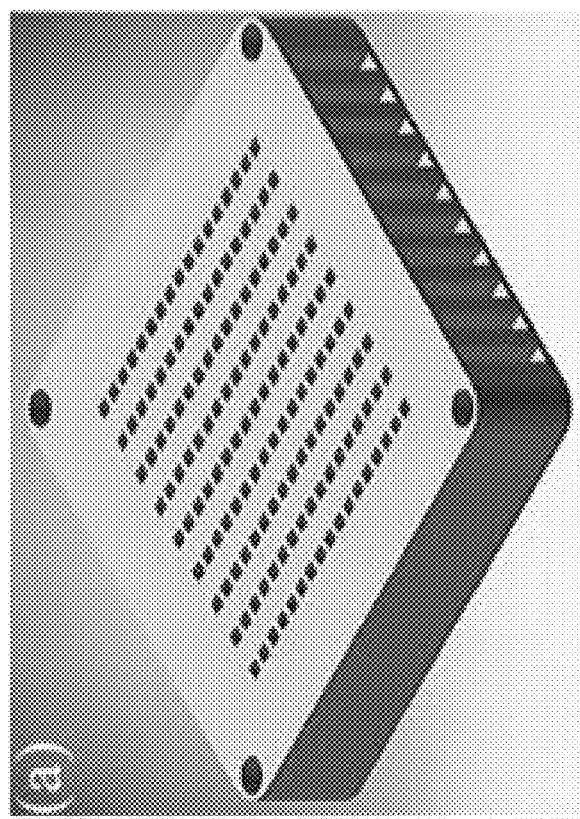
Figure 4D:
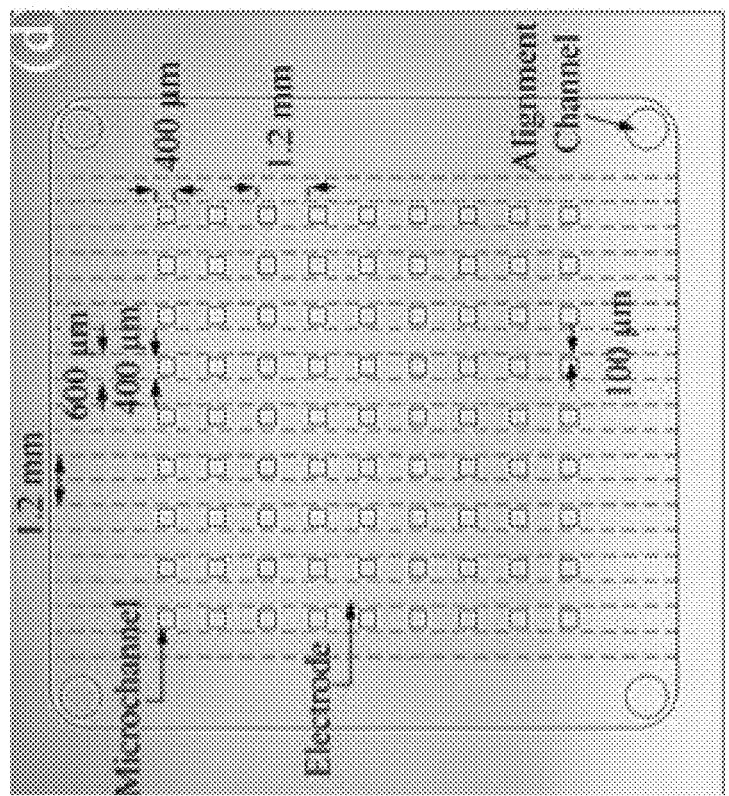
Figure 4C:
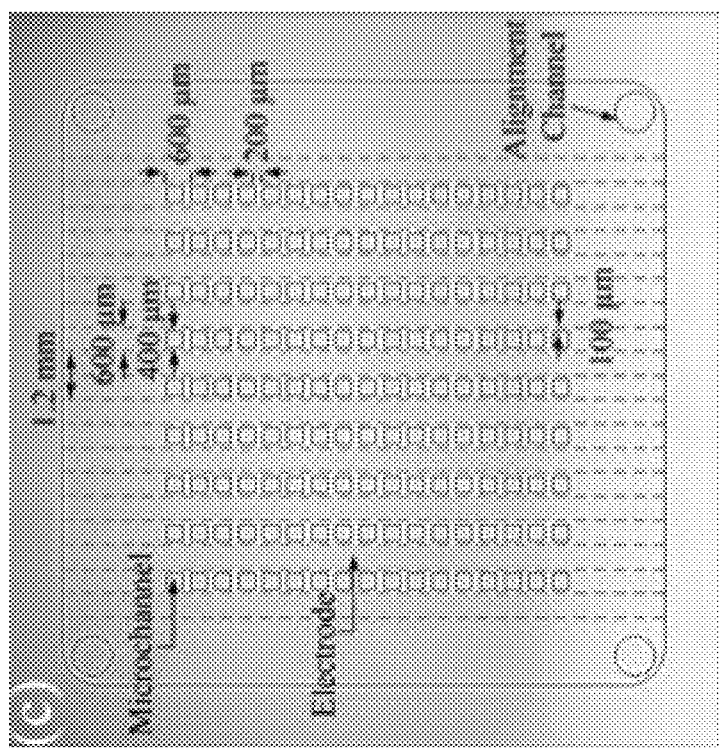

FIGS. 4A-4D illustrate exemplary dimensions of preferred embodiments and details for fabricating the block structure 112, including the microchannels 110 and spaces to insert and electrodes 106 and 108. In the experimental devices, the electrodes were fabricated separately from the block structure and mechanically inserted later. The electrodes can also be printed with the structure. FIG. 4A is an isometric projection of the block structure 112 (see FIGS. 1D-1F), including the microchannels 110 and the gaps and spaces permitting the introduction of the electrodes. The array of microchannels is clearly visible, and the topology of the array can take on numerous forms that will provide the required electric field. For illustrative purposes, a 9×17 array is shown. FIGS. 4C and 4D show, in plan view, the surface of the block structure 112 having different microchannel packing densities, and representative dimensions are given. The pitch (center-to-center spacing) between channels is 0.6 mm for FIG. 4C but 1.2 mm for FIG. 4D. For the specific design of FIGS. 4A-4C, the microplasma channels have an approximately square cross-section (0.6 mm on a side) and the closest distance between the plasma and an electrode is 100 μm. Four holes at the corners of the plate are included for precise alignment of the entire structure (microplasma channel array, diffuser, and air feedstock flow tube) during final assembly. The 3D printing process provides the ability to have microchannels of virtually any cross-sectional geometry, and exemplary cross-sections include circular, oval (elliptical), rectangular and triangular.

FIGS. 5A-5B illustrate the electrode arrays 106 and 108 for the exemplary embodiment of FIGS. 4A-4D, which is consistent with FIGS. 1D-1F. The electrodes 106 and 108 have a comb-like (interdigitated) structure, and can generally have diameters or thicknesses from sub-millimeter to one or more centimeters. FIG. 5A is an isometric projection and FIG. 5B is a plan view of the interdigitated copper electrode design, as the electrodes will be interdigitated (interleaved) when inserted into the array of FIGS. 4A-4D. Electrodes have been fabricated for experimental devices by laser cutting, but other fabrication methods, such as wet etching and powder ablation (combined with photolithography to define the pattern), can also be used.

Figures 6A, 6B:
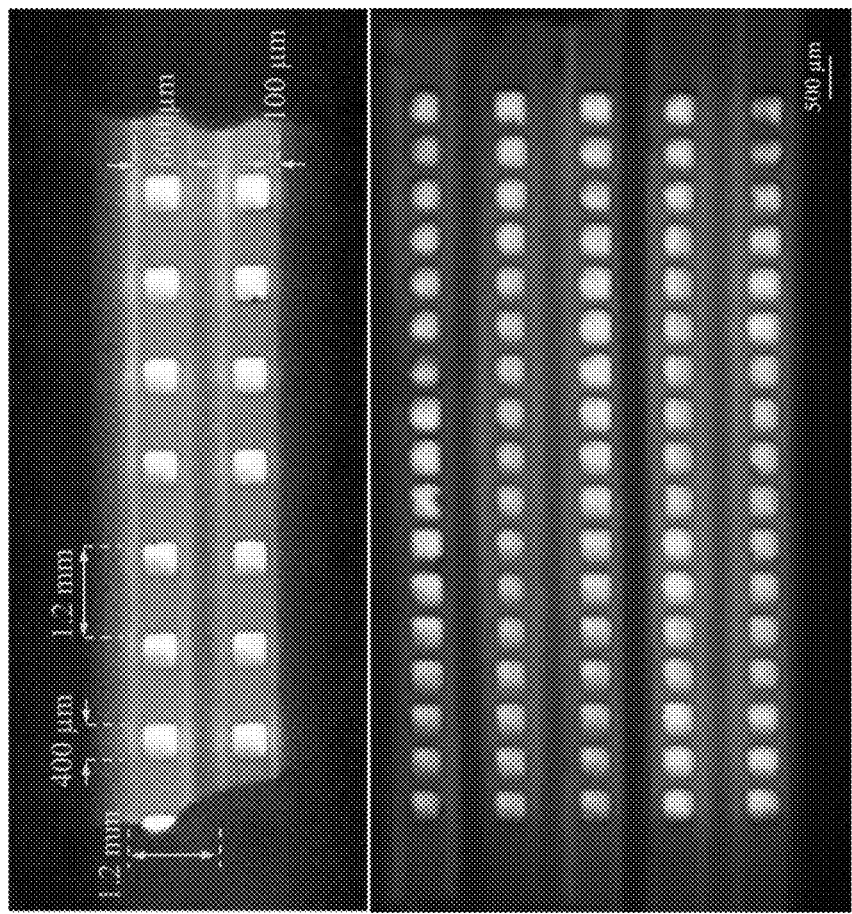
FIGS. 6A and 6B are photographs of example microchannel plasma arrays, fabricated according to FIGS. 4A-4D and operating with room air as the feedstock gas.

FIGS. 6A and 6B are photographs of example microchannel plasma arrays, fabricated according to FIGS. 4A-4D, operating with room air. The arrays were driven by a 20 kHz sinusoid having a peak-to-peak voltage of 5.5 kV. The housing (block structure) of the array structures was fabricated from a polymeric material (low viscosity liquid photopolymer, which produces strong, tough, water-resistant, ABS-like parts) by 3D printing. The optical images in FIGS. 6A and 6B were recorded "end-on"—that is, the plasmas are coming out of the page. FIG. 6A shows an array having the square microchannel cross-section of FIG. 4D in a 2×8 array, while FIG. 6B shows the more densely-packed 5×17 array of FIG. 4C. Each microchannel has a square cross-section of 400×400 μm². The cross-section area of the array can be easily expanded, for example, from 12 mm×12 mm, to 12 cm×12 cm, or larger. The desired size depends upon the specific application. Similarly, a wide range of microchannel lengths (and, therefore, monolithic structure "height" or "thickness") can be utilized, which can create arrays having a total thickness as small as about 3 mm. The microchannel pitch in FIG. 6A is 1.2 mm, while the pitch in FIG. 6B is 600 µm for the rows (along the horizontal coordinate), and 1.2 mm for the columns (vertical coordinate). Experiments demonstrated that an inexpensive microcompressor or fan upstream from the array is able to maintain the gas pressure in the microchannels and diffuser at 785 Torr which is sufficient to produce a flow rate of at least 0.5 slm. Also, the luminosity of the plasmas across the array is nearly uniform, although a loss of intensity at the edges of the array is evident. The images of FIGS. 6A and 6B are representative of those acquired over numerous experiments conducted to show that large arrays of microplasmas can be formed in room air.

The effectiveness of the arrays of FIGS. 6A-6B (as well as other experimental embodiments of the invention) have been tested in numerous experiments. For example, FIGS. 7A-7C illustrate the results of experiments in which $E.\ coli$ bacteria have been deactivated through exposure of the microorganism to the arrays of FIGS. 1D-6B. FIGS. 7A and 7B are illustrative images recorded for initial bacterial number areal densities of $3.58 \times 10^3$ cm$^{-2}$ and 35.8 cm$^{-2}$. FIG. 7C is a photograph in plan view of an agar petri dish that has been exposed to the microplasma array for different exposure times: 10, 30, and 60 s. A remarkable aspect of these results is that the active area for the arrays of these experiments was only approximately 55 mm$^2$, whereas the surface area of the Petri dish is 64 cm$^2$. That is, the surface area of the plasma array is only 0.9% of the area of the Petri dish. The array was not moved during the exposure period and yet the entire surface of the dish is disinfected because of the diffusion of excited atoms and molecules (as well as radicals) over the surface of the colonized agar.

Figure 8:
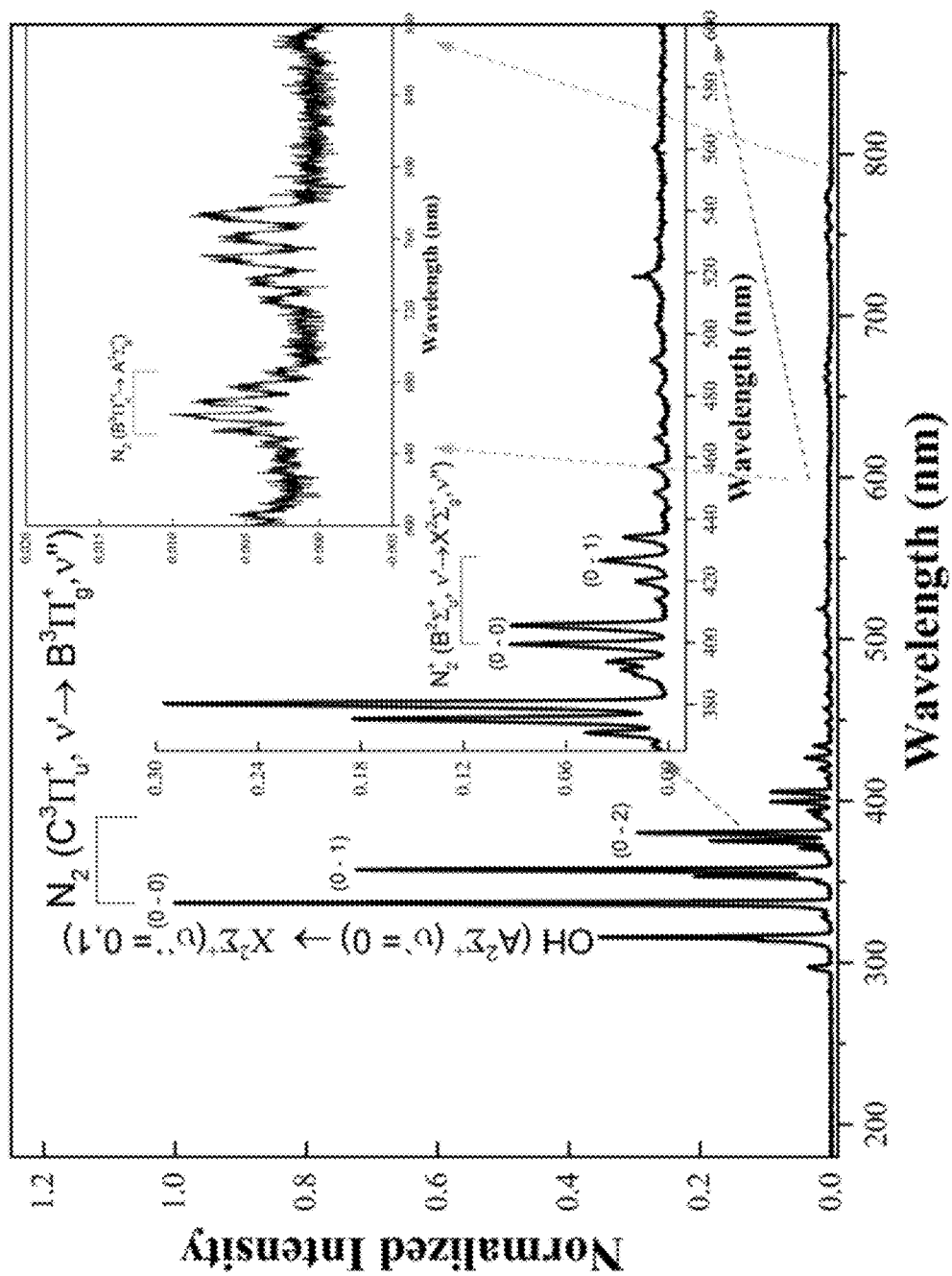
FIG. 8 shows the emission spectrum of microplasma jets, produced by experimental devices in the ultraviolet and visible and recorded over the 180-880 nm spectral region.

FIG. 8 shows the emission spectrum of microplasma jets, generated by experimental devices and recorded over the 180-880 nm spectral region. The insets in FIG. 8 show emission from 360 nm to 600 nm, and 600 nm to 800 nm. This spectrum shows several features of interest, including the presence of the A-X emission band of the hydroxyl radical (OH) at 308 nm. This excited molecule (e.g., OH(A)) has an internal energy of almost 4 eV. Electronically-excited nitrogen molecules are also produced by the microplasmas, and both species have more than sufficient internal energy to deactivate $E.\ coli$ and other pathogens of interest in a medical environment.

FIGS. 9A-9F illustrate a preferred device 902 that provides microplasma jets emerging from outlets of the microchannel array at a plurality of surfaces 118a-118e of the monolithic housing 112. Other portions of the device 902 are labelled with reference numbers from FIGS. 1A-1F. The electrodes are encapsulated behind each face and are, therefore, not shown in FIGS. 9A-9F, but can be arranged as in FIGS. 1A-1F, with opposing electrode arrays arranged around microchannels for each surface 118a-118e. A central volume provides flow for plasma medium to the microchannels in the surfaces 118a-118e, which can be formed as an integrated and monolithic structure or can be joined together after formation of individual arrays of microchannels for each surface 118a-118e.

Figure 10:
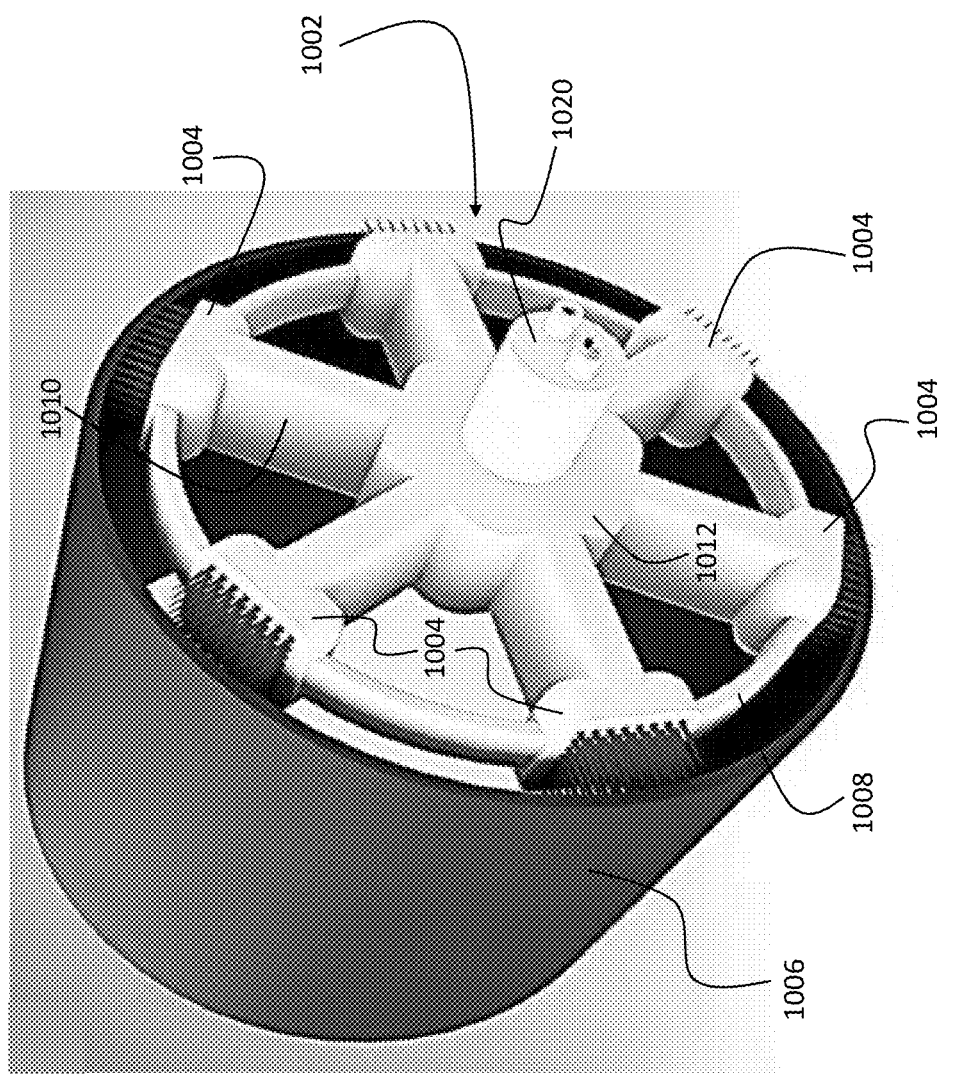
FIG. 10 illustrates a preferred device configured for the deactivation of biofilms in municipal water systems.

FIG. 10 illustrates a preferred device 1002, especially suited for the deactivation of biofilms in municipal water systems. A plurality of plasma jet devices 1004 (for example consistent with the device 102 (FIGS. 1A-1C) or 104 (FIGS. 1D-1F)) are arranged in a Ferris-wheel pattern in which several microplasma jet arrays rotate around a common axis. An outer circumference of the device 1002 is slightly smaller than a water pipe 1006 by a distance set to optimize the interaction of radicals from plasma jets with biofilms on an inner surface of the pipe. This separation is expected to be at least a few mm but preferably no more than 5-10 cm. Circumferential supports 1008 between the devices 1004 provide structural rigidity. Radial arms 1010 extend from a hub 1012 allowing the jet arrays to rotate about a common axis. The radial arms 1010 are designed so as to provide airflow and power lines to the plasma jet devices 1004. A low speed electric motor (not shown) serves to rotate the arms 1010 and the jet arrays 1004 by means of a threaded rod that is coaxial with the hub 1012. A central housing portion 1020 provides ports for providing power to the motor and airflow for generating plasma. Consequently, the rotation of the assembly of FIG. 10 is able to treat the entire inner circumference of the pipe 1006 because, in a preferred embodiment, the inner surface of the hub pipe is threaded, and the thread pattern matches that of a rod that is coaxial with the hub. Therefore, as the threaded rod is rotated by an electric motor, each of the jet arrays on the Ferris wheel structure traces out a helix of exposed area on the interior of the water pipe. Through the choice of the dimensions of the arrays, the thread pitch on the axial rod, and the speed of rotation, the plasma jet devices 1004 can uniformly irradiate the entire interior surface of the pipe. Experiments, discussed below, have shown that exposing biofilms (produced in drinking water transport systems) to the arrays of the invention does, indeed, destroy biofilms. Therefore, the system of FIG. 10 is capable of removing or thinning biofilms on the interior surface of municipal or residential water piping or, alternatively, disinfecting the biofilms without removing the biofilms. The latter requires smaller treatment times.

Figure 11A:
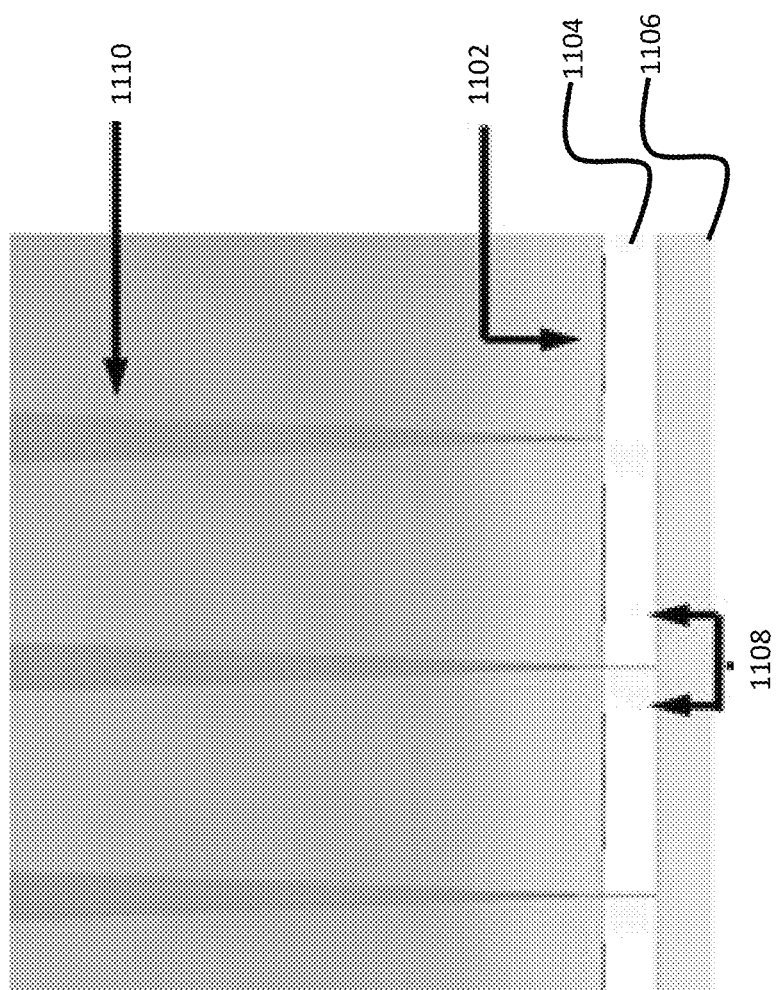
FIGS. 11A-11C illustrate the use of a ground plane for an array, having the form of a static ground electrode array.
Figures 11B, 11C:
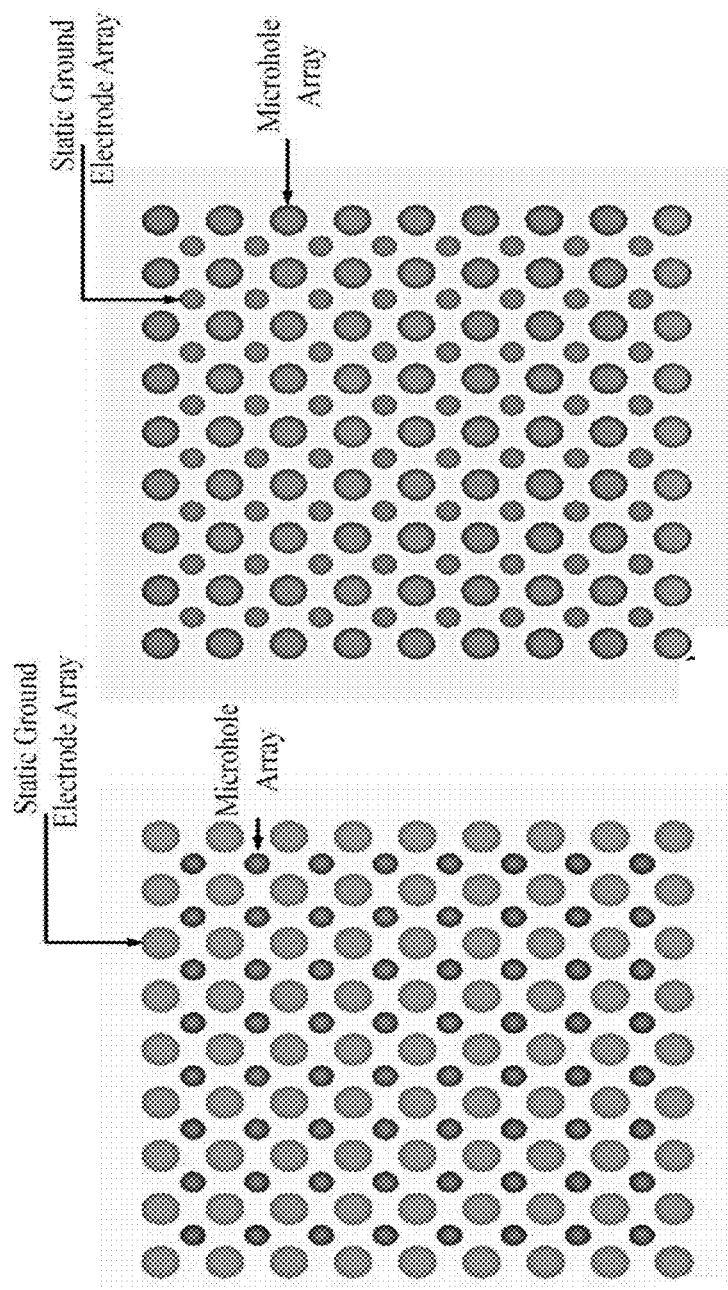

The electrical properties of microplasma jets can be time-varying because electrical ground is often not well defined which can, in turn, affect the plasma—substrate interaction. Control of the produced plasma, and the reactive species delivered to a substrate can be improved through the use of a static ground electrode array placed a fixed distance from the array exit plane of the devices of FIGS. 1A-1F, for example. FIGS. 11A-11C illustrate the use of a ground plane in the form of a static ground electrode array 1102. Considered with FIG. 11A, FIG. 11B shows that the positions of the elements of the ground plane electrode array 1102 are off-set with respect to the axis of the jets in the array, while in FIG. 11C the position of the elements are aligned with the axis of each plasma jet. The different alignments of the elements of the ground plane electrode array 1102 with respect to the jet arrays offer control over the plasma parameters such as the electron density and peak (and time-averaged) gas temperature. The position of the ground is controlled by a non-conductive support 1104 (produced directly by 3D printing) so as to correspond in position to the plasma jets of an array according to the embodiments of FIGS. 1A-6B, or the 9A-9C embodiments. A substrate 1106 to be treated is placed behind the static ground electrode array, and the distance can be fixed by a spacer or by the thickness of the non-conductive support 1104. The non-conductive support includes an array of holes 1108 aligned with plasma jets 1110. The reactive species produced by the microplasma air jet array diffuse along the gas flow direction through the microhole array 1108 and into the substrate treatment area. The holes 1008 can also be offset from the plasma jets 1110, with the plasma jets 1110 instead being aligned with the static ground array. This provides a measure of control over the plasma and permits the reactive species (excited atoms and molecules or radicals) produced by the plasma to migrate through the holes 1108 and treat the substrate 1106.

Figure 12A:
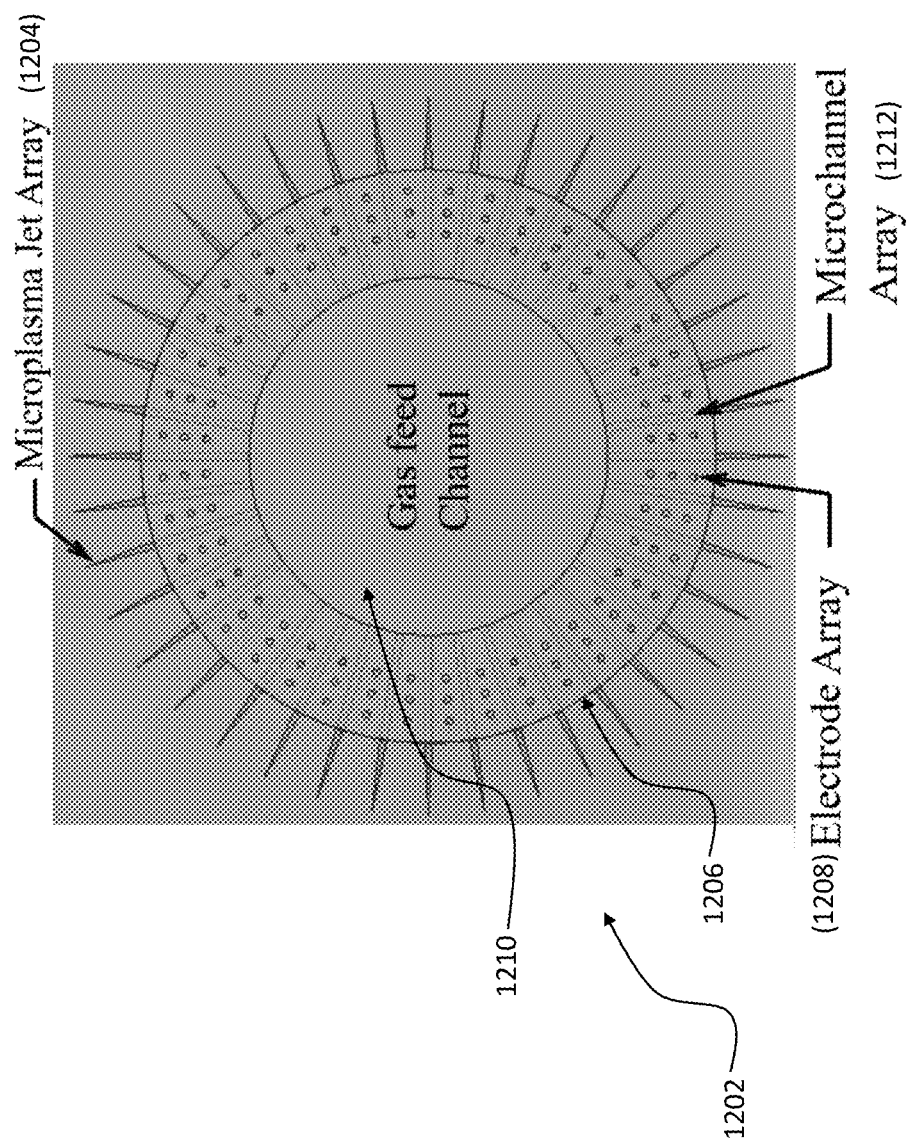
FIGS. 12A-12C illustrate another preferred device configured for treating water supply or drainage pipes.
Figure 12B:
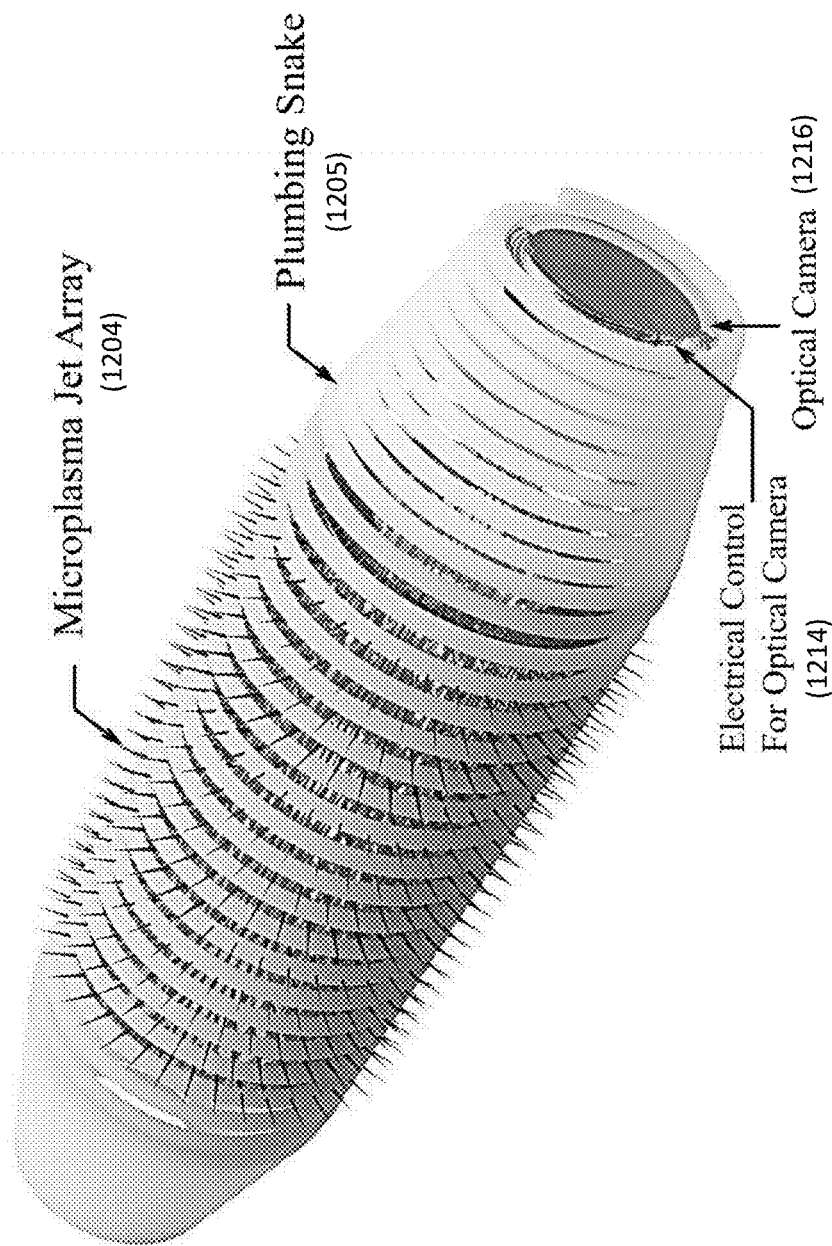
Figure 12C:
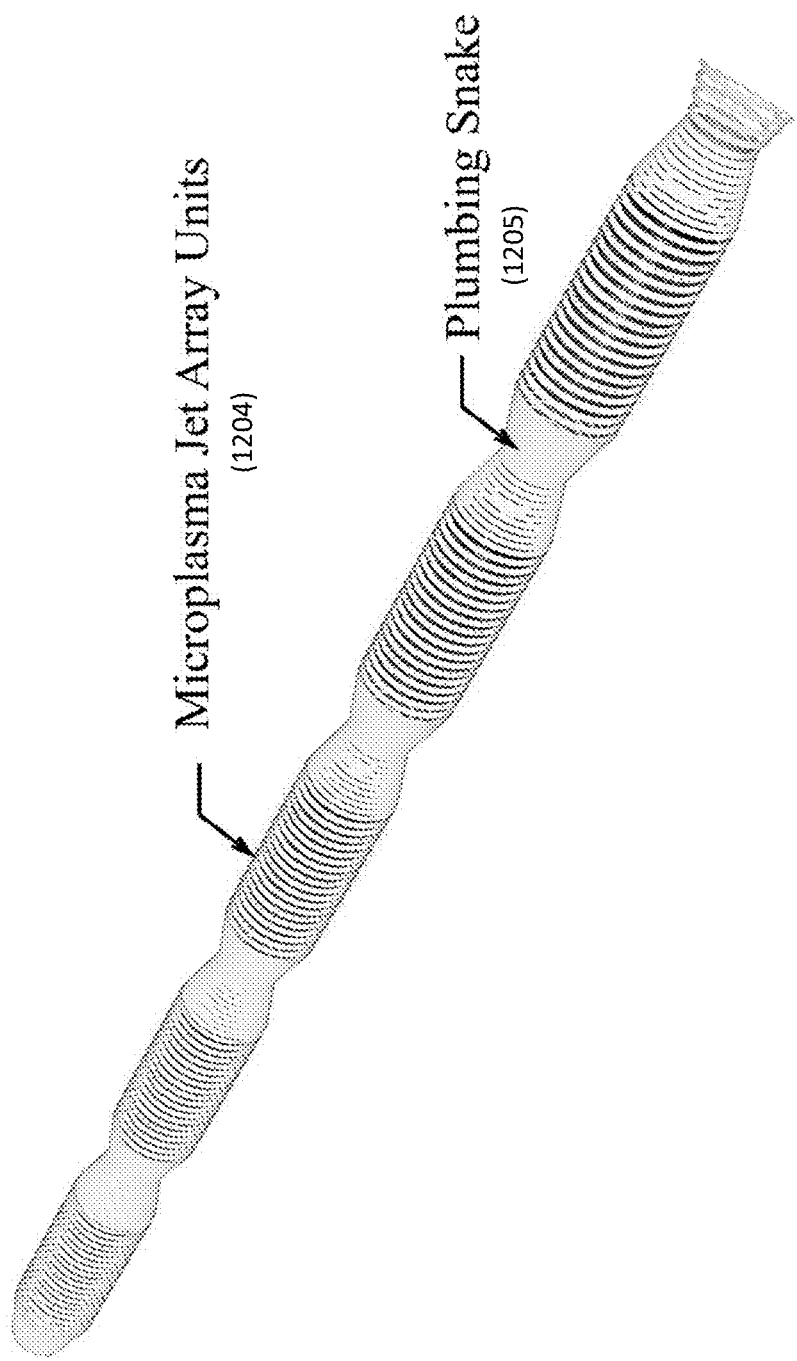

FIGS. 12A-12C illustrate another preferred device 1202 for treating water drainage or supply pipes. The device 1202 is designed so as to integrate microplasma jet arrays with a modified "snake" normally used in the plumbing industry for other purposes, such as imaging or removing clogging materials in pipes. This embodiment is designed specifically for the treatment of biofilms or pathogens present in residential or commercial water systems for which the diameter of the piping is considerably smaller (typically ¼" to more than 2" in diameter) than that in municipal systems. In this situation, accessing the interior surface of the pipes has been a challenge. However, the spatial scale of microplasma jet arrays allows for this environment to now be accessed readily. To this end, the device 1202 includes microplasma jet arrays 1204 having a cylindrical geometry in which the plasma jets are directed radially outwards, and are integrated into a snake 1205. Each cylindrical array is fabricated within a tube 1206 in which the wall of the tube contains an array of electrodes 1208 for powering the individual microplasma jet arrays. Furthermore, the center 1210 of the tube 1206 permits air to flow to each of an array of microchannel 1212, there to be transformed into plasma. Along the axis of the tube, electrical lines and an optical fiber 1214 can also be positioned, as seen in FIG. 12. The electrical lines provide power to the microplasma arrays and the optical fiber is connected to a small CCD camera 1216 which is located at the distal end of the snake. The camera is advantageous for monitoring the interior of the pipe as the snake is navigated through the plumbing system. FIG. 12C shows that multiple arrays 1204 can be integrated into a snake 1205 at periodic locations along the snake's length. The number of arrays 1204 incorporated into a snake 1205 depend on the length of pipe to be treated and the desired treatment time. Multiple such snakes can be employed simultaneously to treat separate sections of a large water system. The integration of multiple arrays into a single snake serve to maintain the overall flexibility of the snake 1205 along its length while providing a long (axial) distance of microplasma coverage.

Simulated Drinking Water Biofilm Disintegration Experiments.

Additional experiments were conducted to test the efficacy of plasma devices to disintegrate water biofilms. In the experiments, simulated drinking water biofilms, grown from groundwater, were exposed to He plasma jets from a 9×9 array and the exposure had the effect of severely eroding the biofilms and deactivating the organisms they harbor. Air can now be used as the feedstock gas, and will provide a different chemistry than plasma generated with the He medium. In-situ measurements of biofilm structure and thickness with an optical coherence tomography (OCT) system show the biofilm thickness to fall from 122±17 μm to 55±13 μm after 15 minutes of exposure of the film to the microplasma jet array, when the plasmas are dissipating a power density of 58 W/cm$^2$. All biofilms investigated vanish with 20 minutes of exposure. Confocal laser scanning microscopy (CLSM) demonstrates that the number of living cells in the biofilms declines by more than 93% with 15 min. of biofilm exposure to the plasma arrays. Concentrations of several oxygen-bearing species, generated by the plasma array, were found to be 0.4-21 nM/s for the hydroxyl radical (OH), 85-396 nM/s for the $^1O_2$ excited molecule, 98-280 μM for $H_2O_2$, and 24-42 μM for $O_3$ when the power density delivered to the array was varied between 3.6 W/cm$^2$ and 79 W/cm$^2$. The data demonstrate the potential of the present devices as a previously-unavailable tool for controlling, through disruption and removal, mixed-species biofilms prevalent in drinking water distribution systems. Furthermore, the biofilm erosion rates are expected to be comparable to, or larger than, those cited above for helium as the feedstock gas.

An extensive suite of diagnostics examined the deformation and removal of the biofilms during plasma treatment, as well as the reactive oxygen species produced by the interaction of the helium (He) plasma micro-columns with room air. Specifically, optical coherence tomography (OCT) shows that the thickness of simulated water biofilms falls from a mean value of 122±17 μm to 55±13 μm after 15 minutes of exposure to a microplasma array operating at a modest power density (58 W/cm$^2$). With 20 minutes of exposure at the same power density, the biofilms vanish. Faster biofilm removal rates are readily available with larger dissipated power densities (up to 78 W/cm$^2$ in the present experiments). Furthermore, analysis of treated biofilms by confocal laser scanning microscopy (CLSM) reveals that the number of living cells remaining in the biofilm (following 15 minutes of exposure to the plasma) is reduced by 93% with respect to the control. Concentrations of the hydroxyl radical (OH), singlet oxygen ($^1O_2$), hydrogen peroxide ($H_2O_2$), and ozone ($O_3$) produced by the microplasmas were measured by liquid chromatography or colorimetry (in the case of hydrogen peroxide), and it is these species that appear to be primarily responsible for the destruction of the biofilms and the deactivation of the pathogens they contain. Aside from the sensitivity of the present experiments (nanomolar per second) in measuring the generation rates for hydroxyl radicals and singlet oxygen produced by the microplasmas, the primary significance of the results is the demonstration of an effective tool with which the growth of biofilms in drinking water distribution networks can be mitigated. Furthermore, the insertion of microplasma arrays of cylindrical geometry into commercial or residential plumbing systems, in a fashion similar to that of conventional plumbing snakes, is feasible.

9×9 Plasma Jet Array.

Several experimental arrays were consistent with FIGS. 1D-1F. The gas entry tube was 4 mm in diameter. The feedstock gas (He, 99.99%) encounters the microchannel diffuser and a shallow plenum region which serve the purpose of minimizing turbulence and directing gas equally to each of the square cross-section microchannels. This entire structure was fabricated in a transparent polymer (ABS (Acrylonitrile butadiene styrene) or ABS-like material) by 3D printing. The electrode arrays having the multi-finger design of FIGS. 5A and 5B were machined in copper. When the electrodes were installed and powered, this device generated a 9×9 array of microplasma columns that emerged from the lower face of the device, producing visible plumes extending approximately 1 mm into room air.

The full 9×9 array of microchannels had an overall area of 125.4 mm$^2$ (1.25 cm$^2$). The pitch (center-to-center spacing) between adjacent channels was 1.2 mm along both the horizontal and vertical axes of the two-dimensional array which defines the areal packing density of the array as 88 channels/cm$^2$. The arrays were fabricated with a 3D printing tool having a spatial resolution of 50 μm.

Preparation of Simulated Drinking Water Biofilms.

Biofilms were grown on polyvinyl chloride (PVC) coupons from a groundwater source of drinking water in Urbana-Champaign, Ill. (USA). Treated by a greensand filter, this water was found to contain 1.65±0.08 mM Ca$^{2+}$, 1.16±0.01 mM Mg$^{2+}$, and 1.04 mM Na$^+$, and its measured hardness is 281±8 mg/L. The total organic content (TOC) of the groundwater is 1-1.6 mg/L, and the pH is in the range of 7.5-7.8. Standard growth procedures were followed. PVC coupons (RD 128-PVC, BioSurface Technologies Corporation, Bozeman, Mont.) served as the substrate for the biofilms. After placing the coupons into CDC reactors (CBR 90-2, Biosurface Technologies Corporation), groundwater was pumped continuously into the reactors and biofilm development took place under shearing conditions because of continuous stirring within the reactors at 125 rpm, which corresponds to an Re of 2384. No extraneous nutrients or microorganism strains were introduced to the reactors, and the biofilms were allowed to develop undisturbed for 10 months prior to the characterization and plasma treatment experiments.

Plasma Treatment of Biofilms.

Figure 13:
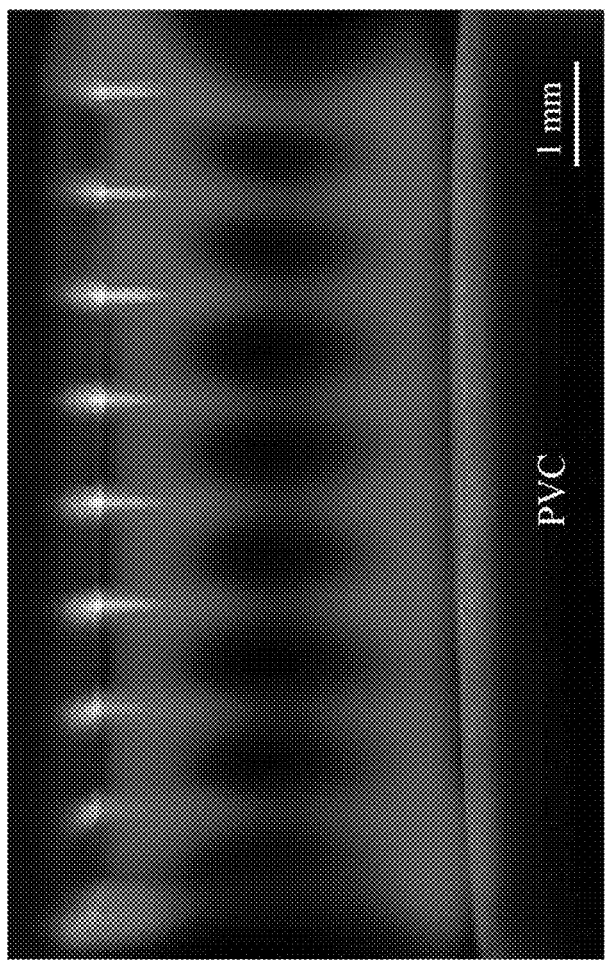
FIG. 13 is a side view image of the optical emission emanating from a microplasma jet array during the irradiation (in room air) of a biofilm coupon.

The array was driven by a 20 kHz sinusoidal waveform having an RMS value of 1.2 kV. Helium gas flow was maintained at 0.25 L/min/microchannel (approximately 20 l/min. total flow rate) and the exit face of the array was situated 4 mm from a PVC coupon onto which a biofilm had been grown. In total, seven biofilm coupons were examined in this study. FIG. 13 is a side view of the optical emission recorded with a Cannon camera (Canon 5D Mark III) during the irradiation (in room air) of one of the biofilm coupons. This image illustrates vividly the interaction of the He plasma with air to produce molecular radicals, ions, and excited species. Once the microplasmas emerge into room air, the fluorescence of the He plasma columns (which was red in the original color image) is transformed into (blue in the original color image) emission as a result of the Penning ionization of the nitrogen molecule by the He ($2^3S$) metastable species. The B-X electronic transition of the $N_2^+$ ion is responsible for the fluorescence evident above the biofilm coupon (which was violet/blue in the original color image). Note that the breadth of $N_2^+$ resultant emission profiles is greater than that of the He microplasmas, owing to the diffusion of He metastables into the cold surrounding gas.

Biofilm Imaging By Optical Coherence Tomography (OCT) and Confocal Laser Scanning Microscopy.

All biofilms were examined in situ, both prior to and after plasma treatment, by OCT. A spectral domain OCT system, emitting low-coherence light with a central wavelength of 1322 nm and a bandwidth of 106 nm, offers an axial and transverse resolution of 4.2 µm and 3.9 µm, respectively, in air. For each biofilm sample, cross-sectional images having a volume of 3.1 mm (transverse dimension)×2.1 mm (depth)×4 mm were recorded at three locations on the film, and 600 images were captured for each biofilm coupon. Seventy cross-sectional images were selected randomly for further analysis. Each of these images was processed to suppress or eliminate background noise. Also, the mean thickness of all biofilms was determined by analyzing the gray scale gradient through automatic thresholding.

After the completion of the OCT scans, the same biofilm samples were stained following the protocol of the LIVE/DEAD BacLight™ Bacterial Viability Kit (Thermo Fisher Scientific). This assay determines the viability of the cell membrane. Living cells were stained green with SYTO 9 while dead cells were stained red (propidium iodide) for subsequent evaluation by CLSM. Images were acquired with a Leica SP8 laser scanning confocal microscope in which photoexcitation occurs at 488 nm (Ar ion laser) and the detection wavelengths are 500 nm and 635 nm for SYTO 9 and propidium red, respectively. Final images were produced from the microscope data by LAS X software offered by Leica Microsystems.

Detection of Microplasma-Produced Reactive Oxygen Species.

Knowledge of the absolute concentrations of several critical oxygen-bearing radicals and excited species, such as OH, $^1O_2$, $H_2O_2$, and $O_3$, is essential to assessing the efficacy of microplasmas for the deactivation of bacterial pathogens. To this end, tests were conducted in which a beaker 3.5 mm in height was situated immediately beneath the exit face of the microplasma arrays. The beaker contained a 10 mL solution of phosphate-buffered saline solution (PBS; pH=7.4) and 100 µM of either phenol (99%, Acros Organics) or furfuryl alcohol (FFA; 98%, Acros Organics), the latter of which serve as a diagnostic of OH (phenol) or $^1O_2$ (FFA). After the appropriate solution was exposed to the He plasma jets emerging into room air, samples were withdrawn and the decay of the desired probe was detected by liquid chromatography with an Agilent series 1200 HPLC chromatograph having an Eclipse Plus C18 (3.5 µm) column. Separation was performed with water and acetonitrile with a ratio of 50:50 for phenol and 40:60 for FFA, and the flow rate and injection volume were fixed at 0.3 mL/minute and 20 µL, respectively. The detection wavelengths for phenol and FFA were 268 nm and 216 nm, respectively.

The concentration of the designated probe was calculated on the basis of the standard curve for the same probes in PBS. For the OH radicals generated by the microplasma array, the concentration in the beaker solution was determined from the decay of phenol in solution and is given by the product of the rate constant for the phenol-OH interaction ($1.4 \times 10^{10}$ $M^{-1}s^{-1}$) and the phenol concentration. Similarly, the $^1O_2$ concentration was determined from the product of the $^1O_2$-FFA interaction rate constant ($1.4 \times 10^8$ $M^{-1}s^{-1}$) and the FFA concentration. Measurements of the hydrogen peroxide concentration were facilitated by a colorimetric test kit (CHEMets Visual Kit). Hydrogen peroxide oxidizes ferrous iron to the ferric state, resulting in the formation of a red thiocyanate complex. By comparing the colors of the test samples with those of standard samples (provided by the test kit), the concentrations of $H_2O_2$ in the test samples were determined. The minimum detectable value was 1.5 µM. Finally, the concentration of ozone dissolved in solution was measured with a second test kit (HACH OZ-2 (2064400)). Each test was performed at least three times, in order to obtain a statistically significant result.

Experimental Results.

OCT images of the biofilms were recorded in situ, both prior to exposure to the He microplasma array and at several points during the treatment process.

Figures 14A, 14B, 14C, 14D:
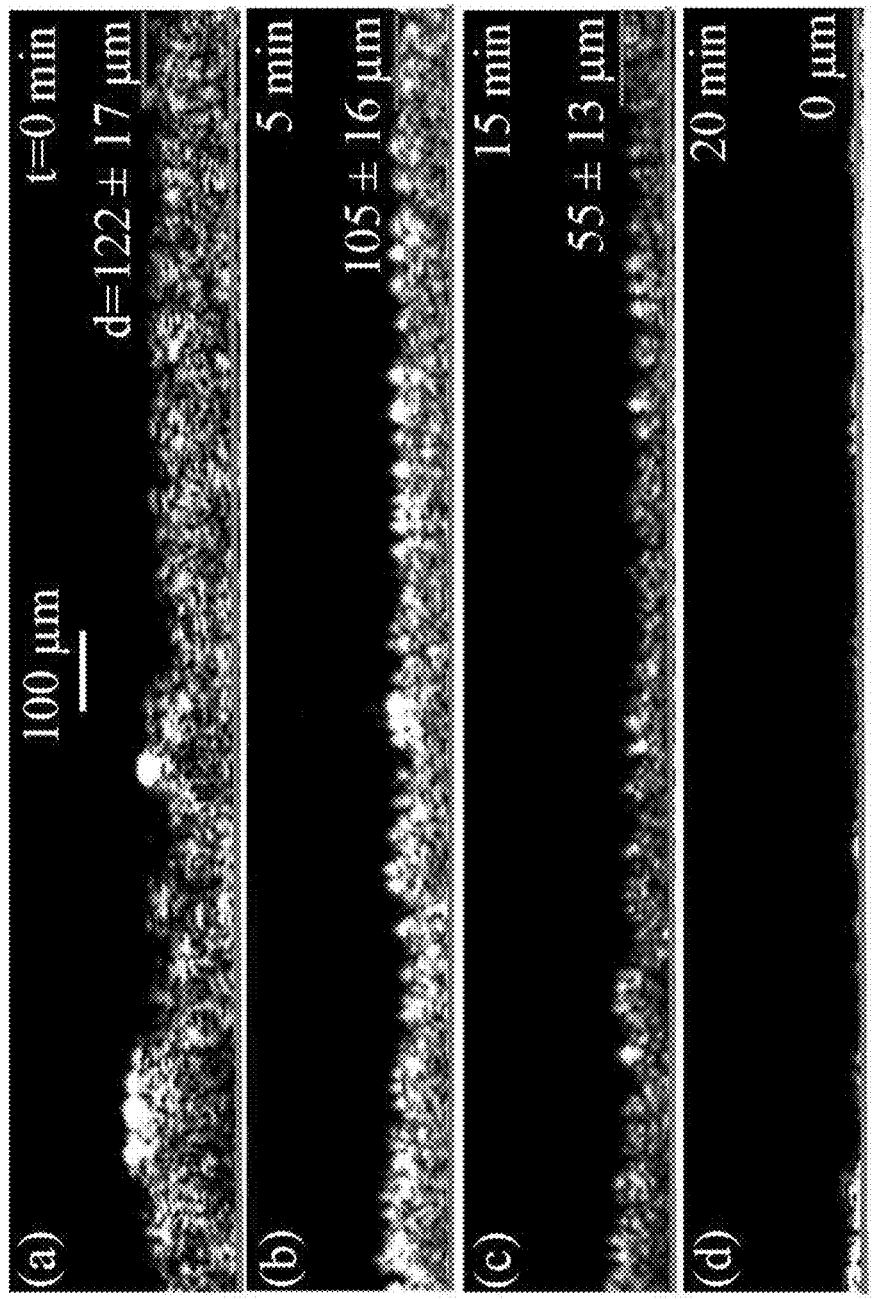
FIGS. 14A-14D are cross-sectional images showing exemplary reductions in biofilm thickness achieved through treatment with an experimental microplasma jet array of the invention.

Representative results are shown in cross-section in FIGS. 14A-14D. FIG. 14A is a profile of the film prior to plasma treatment and FIGS. 14B-14D illustrate the impact on the structure and average thickness of the film after exposure to the plasma array for time periods (t) of 5, 15, and 20 minutes. Throughout these tests, the electrical power delivered to the array was fixed at 3.4 W. In each image of FIG. 14, the dashed horizontal line indicates the boundary between the biofilm and the surface of the PVC coupon. Note that the biofilm thickness decreases from an initial value of 122±17 µm (where the uncertainty represents one standard deviation) to 55±13 µm after 15 min. of exposure to the plasma array. This represents a decline in thickness of 55% and a linearized biofilm erosion rate of 4.5 µm/min. After 20 minutes of plasma treatment, no biofilm is detectable to within experimental uncertainty. The temporal rate of biofilm removal by the microplasma jets is decidedly non-linear, which is attributable to the time required for the radicals, and excited species, produced by the microplasma jet columns to diffuse through one atmosphere of air and reach the coupon. Confocal laser microscopy was also conducted, and confirmed the FIGS. 14A-14D results, indicating a dramatic drop of biofilm thickness after 15 minutes of exposure. Before 20 minutes of exposure, all of the biofilms investigated vanished. Depth-resolved studies of green (SYTO 9) and red (propidium red) photoemission generated by CLSM were conducted for both untreated biofilms and those exposed for 15 min. to microplasmas and the species they produce in air. These results showed that green channel (SYTO 9) fluorescence decreases by approximately 90% when the biofilms are exposed to plasma for 15 minutes. Similarly, the red fluorescence declines by 80% during that same time period because of the rapid erosion of the biofilm by the plasma array. The disintegration of the biofilms was also experimentally correlated with the concentrations of reactive species generated by the microplasma jet array in the liquid phase by measuring the degradation kinetics of the probe chemicals.

The experiments showed that exposure of simulated drinking water biofilms to the excited species, radicals, and ultraviolet radiation produced by a 9×9 array of microplasma eroded and then completely removed the films while deactivating the cells they contain. Measurements of biofilm thickness by OCT demonstrate that 122 μm thick films are removed entirely by 20 minutes of exposure to the plasma array. Combined with the observation that the number of living cells in the biofilms falls by >93% with 15 minutes of exposure, these results indicate that arrays of low temperature plasma jets offer an inexpensive and effective tool with which the growth of biofilms in drinking water distribution systems can be mitigated or eliminated.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A microplasma device for treatment of a surface or object, the device comprising:
   an array of elongate microchannels formed in a polymer, plastic or ceramic body having tolerance to ozone and other radicals or excited molecular species formed when plasma is generated from air in the microchannels, the microchannels including inlets configured to accept an air feed, and an array of outlets on an outer surface of the polymer, plastic or ceramic body configured to direct an array of plasma jets toward the surface or object;
   an array of electrodes within the polymer, plastic or ceramic body configured to ignite and maintain plasma in the microchannels and being isolated by a polymer, plastic or ceramic wall from the microchannels;
   an air supply intake feed;
   a diffuser between the air supply intake and the array of elongate microchannels, the diffuser being physically separated from the array of elongate microchannels and configured to apportion the incoming air approximately equally among the microchannels while minimizing turbulence.

2. The device of claim 1, wherein the polymer, plastic or ceramic body is fabricated from ABS (Acrylonitrile butadiene styrene).

3. The device of claim 1, further comprising an entry tube in fluid communication with the array of elongate microchannels and a fan or pump to draw air into the entry tube with sufficient pressure to produce plasma jets extending out from the outlets.

4. The device of claim 1, further comprising a power supply to power the electrodes to create an electric field strength sufficient to generate plasma and radicals from air.

5. The device of claim 1, wherein the electrodes are arranged to generate an electric field oriented perpendicular to the flow of plasma medium through the microchannels.

6. The device of claim 1, wherein the electrodes are arranged to generate an electric field oriented parallel to the flow of plasma medium through the microchannels.

7. The device of claim 1, wherein the array of microchannels comprise square, cylindrical, octagonal, hexagonal, triangular, or rectangular cross-section microchannels.

8. A microplasma device for treatment of a surface or object, the device comprising: an array of elongate microchannels formed in a polymer plastic or ceramic compatible with 3D printing and having tolerance to ozone and other radicals or molecular excited species formed when plasma is generated from air in the microchannels and having an electric field tolerance of at least 3 kV/mm, the microchannels including inlets configured to accept an air feed, and outlets configured to direct plasma jets toward the surface or object;
   an array of electrodes within the polymer, plastic or ceramic configured to ignite and maintain plasma in the microchannels and being isolated by the polymer, plastic or ceramic from the microchannels; and
   a supply intake for providing a plasma medium into the microchannels.

9. The device of claim 8, wherein the array of microchannels comprise square cross-section microchannels.

10. A microplasma device for treatment of a surface or object, the device comprising:
    an array of elongate microchannels formed in a polymer, plastic or ceramic compatible with 3D printing and having tolerance to ozone and other radicals or molecular excited species formed when plasma is generated from air in the microchannels an having an electric field tolerance of at least 3 kV/mm, the microchannels including inlets configured to accept an air feed, and outlets configured to direct plasma jets toward the surface or object, wherein the array of microchannels and outlets are configured in a Ferris wheel arrangement to treat an inner surface of a pipe or chamber;
    an array of electrodes within the polymer, plastic or ceramic configured to ignite and maintain plasma in the microchannels and being isolated by the polymer, plastic or ceramic from the microchannels; and
    a supply intake for providing a plasma medium into the microchannels.

11. A microplasma device for treatment of a surface or object, the device comprising:
    an array of elongate microchannels formed in a polymer, plastic or ceramic having tolerance to ozone and other radicals or molecular excited species formed when plasma is generated from air in the microchannels, the microchannels including inlets configured to accept an air feed, and outlets configured to direct plasma jets toward the surface or object;

an array of electrodes within the polymer, plastic or ceramic configured to ignite and maintain plasma in the microchannels and being isolated by the polymer, plastic or ceramic from the microchannels;

a supply intake for providing a plasma medium into the microchannels; and a static ground electrode at a predetermined distance from the outlets.

12. The device of claim 11, wherein the array of electrodes is arranged perpendicular to the longitudinal axes of, and disposed between, microchannels of the array of elongate microchannels.

13. A microplasma device for treatment of a surface or object, the device comprising: an array of elongate microchannels formed in a polymer, plastic, or ceramic compatible with 3D printing having tolerance to ozone and other radicals or molecular excited species formed when plasma is generated from air in the microchannels and having an electric field tolerance of at least 3 kV/mm, the microchannels including inlets configured to accept an air feed, and outlets configured to direct plasma jets toward the surface or object, wherein the polymer, plastic or ceramic consists of a monolithic polymer, plastic or ceramic block;

an array of electrodes within the polymer, plastic or ceramic configured to ignite and maintain plasma in the microchannels and being isolated by the polymer, plastic or ceramic from the microchannels; and a supply intake for providing a plasma medium into the microchannels.

14. The device of claim 13, further comprising a diffuser arranged between the supply intake and the inlets of the array of microchannels.

15. The device of claim 14, wherein the diffuser defines and is separated from inlets of the microchannels.

16. The device of claim 13, wherein the outlets are on a plurality of surfaces of the monolithic polymer, plastic or ceramic block.

17. A municipal water biofilm treatment device, comprising:

a plurality of microplasma devices, each of the microplasma devices comprising an array of elongate microchannels formed within a polymer, plastic or ceramic having tolerance to ozone and other radicals or molecular excited species formed when plasma is generated from air in the microchannels, the microchannels including inlets configured to accept an air feed, and outlets configured to direct plasma jets toward the surface or object;

an array of electrodes within the polymer, plastic or ceramic configured to ignite and maintain plasma in the microchannels and being isolated by the polymer, plastic or ceramic from the microchannels; and a supply intake for providing a plasma medium into the microchannels; and a hub, radial arms extending from the hub to the plurality of microplasma devices and circumferential supports between the plurality of microplasma devices, wherein the hub and radial arms are configured to supply airflow and electrical power to the plurality of microplasma devices.

18. The municipal water biofilm treatment device of claim 17, further comprising a rod and motor for rotating the hub, wherein the rod and hub are threaded to provide rotation and longitudinal movement of the plurality of microplasma devices.

19. A microplasma device for treatment of a surface or object, the device comprising:

an array of elongate microchannels formed in a polymer, plastic or ceramic having tolerance to ozone and other radicals or molecular species formed when plasma is generated from air in the microchannels, the microchannels including inlets configured to accept an air feed, and outlets configured to direct plasma jets toward the surface or object;

an array of electrodes within the polymer, plastic or ceramic configured to ignite and maintain plasma in the microchannels and being isolated by the polymer, plastic or ceramic from the microchannels;

a supply intake for providing a plasma medium into the microchannel; and a static ground electrode array and holes disposed at a distance from the outlets of the microchannels.

20. The device of claim 19, wherein the holes are aligned with the outlets of the microchannels.

21. The device of claim 20, wherein the holes are offset from the outlets of the microchannels.

22. A water drain or supply biofilm treatment device, comprising:

a plurality of microplasma devices integrated into a plumbing snake, each of the microplasma devices comprising an array of elongate microchannels formed in a polymer, plastic or ceramic having tolerance to ozone and other radicals formed when plasma is generated from air in the microchannels, the microchannels including inlets configured to accept an air feed, and outlets configured to direct plasma jets toward the surface or object;

an array of electrodes within the polymer, plastic or ceramic configured to ignite and maintain plasma in the microchannels and being isolated by the polymer, plastic or ceramic from the microchannels; and a supply intake for providing a plasma medium into the microchannels.

23. The water drain or supply biofilm treatment device of claim 22, wherein the array of elongate microchannels and the array of electrodes are integrated into the wall of a tube.

24. A microplasma device for treatment of a surface or object, the device comprising:

a plurality of arrays of elongate microchannels formed in a polymer, plastic or ceramic having tolerance to ozone and other radicals or molecular species formed when plasma is generated from air in the microchannels, the microchannels including inlets configured to accept an air feed, and outlets configured to direct plasma jets toward the surface or object;

arrays of electrodes within the polymer, plastic or ceramic configured to ignite and maintain plasma in the microchannels and being isolated by the polymer, plastic or ceramic from the microchannels;

a supply intake for providing a plasma medium into the microchannels;

a central volume between the supply intake and the plurality of arrays of elongate microchannels;

plasma jet outlets from the plurality of arrays of elongate microchannels, wherein the plasma jet outlets are in a plurality of surfaces of the polymer, plastic or ceramic and the plurality of surfaces face in a plurality of directions.

* * * * *